(12) United States Patent
Harada

(10) Patent No.: US 12,133,627 B2
(45) Date of Patent: Nov. 5, 2024

(54) ENDOSCOPE AND MOUNTING COMPONENT

(71) Applicant: FUJIFILM Corporation, Tokyo (JP)

(72) Inventor: Takashi Harada, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 36 days.

(21) Appl. No.: 17/374,172

(22) Filed: Jul. 13, 2021

(65) Prior Publication Data

US 2022/0061631 A1    Mar. 3, 2022

(30) Foreign Application Priority Data

Aug. 26, 2020   (JP) ................................. 2020-142537

(51) Int. Cl.
*A61B 1/00*    (2006.01)
*A61B 1/018*   (2006.01)

(52) U.S. Cl.
CPC ........ *A61B 1/0008* (2013.01); *A61B 1/00128* (2013.01); *A61B 1/00137* (2013.01); *A61B 1/018* (2013.01)

(58) Field of Classification Search
CPC .............. A61B 1/0008; A61B 1/00098; A61B 1/00137; A61B 1/018; A61B 1/00128
See application file for complete search history.

(56) References Cited

U.S. PATENT DOCUMENTS 5,730,701 A * 3/1998 Furukawa ............... A61B 1/012
                                                         600/129
2018/0140171 A1* 5/2018 Yamaya .............. A61B 1/00062
(Continued)

FOREIGN PATENT DOCUMENTS

JP    7-265257 A    10/1995
JP    8-140923 A     6/1996
(Continued)

OTHER PUBLICATIONS

Japanese Notice of Reasons for Refusal for Japanese Application No. 2020-142537, dated Aug. 9, 2023, with an English translation.

*Primary Examiner* — Anh Tuan T Nguyen
*Assistant Examiner* — Rynae E Boler
(74) *Attorney, Agent, or Firm* — Birch, Stewart, Kolasch & Birch, LLP

(57) ABSTRACT

Provided are an endoscope and a mounting component which are capable of safely detaching a distal end cap from a distal-end-portion body.

An endoscope includes an operation part that is provided with an operation member; an insertion part that is provided on a distal end side of the operation part and is inserted into an object to be examined; an elevator that is provided in a distal end portion of the insertion part; a distal end cap that is mounted on the distal end portion and has an inner space communicating with a cap opening; an elevating operation wire of which a distal end side is connected to the elevator and which is pushed and pulled in response to operation of the operation member to operate the elevator; a wire channel through which the elevating operation wire is inserted; and a mounting component that is attachably and detachably mounted on the operation part, in which the mounting component has a wire fixing section that mechanically connects the operation member and the elevating operation wire to each other, and a jig section capable of detaching the distal end cap from the distal end portion.

10 Claims, 19 Drawing Sheets

(56) References Cited

U.S. PATENT DOCUMENTS

| | | | |
|---|---|---|---|
| 2018/0317741 A1 | 11/2018 | Yamaya | |
| 2018/0317742 A1* | 11/2018 | Yamaya | ................ A61B 1/0008 |
| 2020/0214544 A1* | 7/2020 | Harada | .............. A61B 1/00042 |
| 2020/0345210 A1 | 11/2020 | Harada | |
| 2021/0068628 A1* | 3/2021 | Yamaya | ............. A61B 1/00133 |

FOREIGN PATENT DOCUMENTS

| | | | |
|---|---|---|---|
| WO | WO 2017/122692 A1 | 7/2017 | |
| WO | WO-2019065580 A1 * | 4/2019 | ......... A61B 1/00039 |
| WO | WO 2019/163401 A1 | 8/2019 | |

* cited by examiner

FIG. 4A
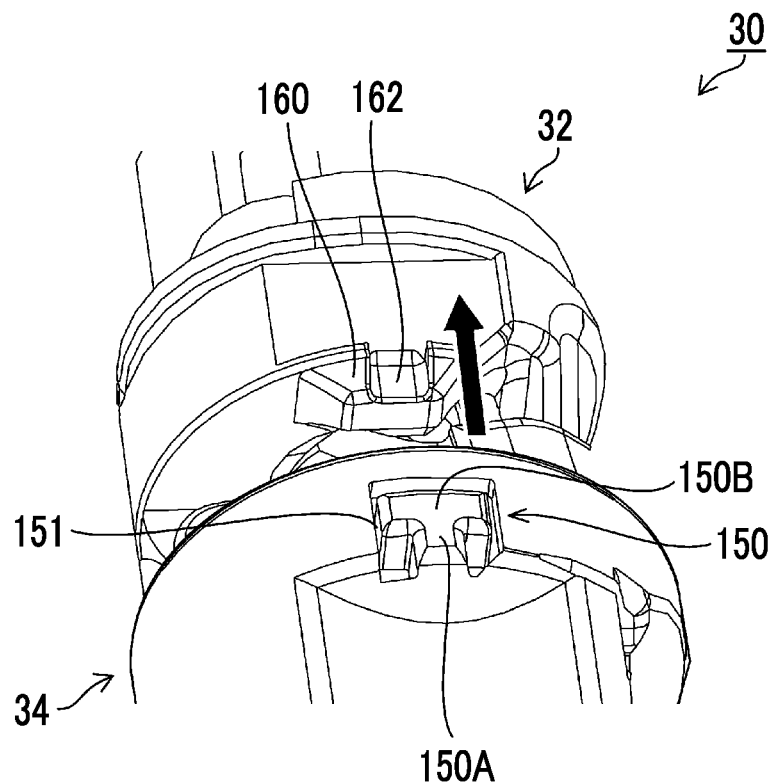
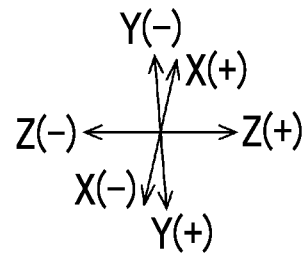
FIG. 4B
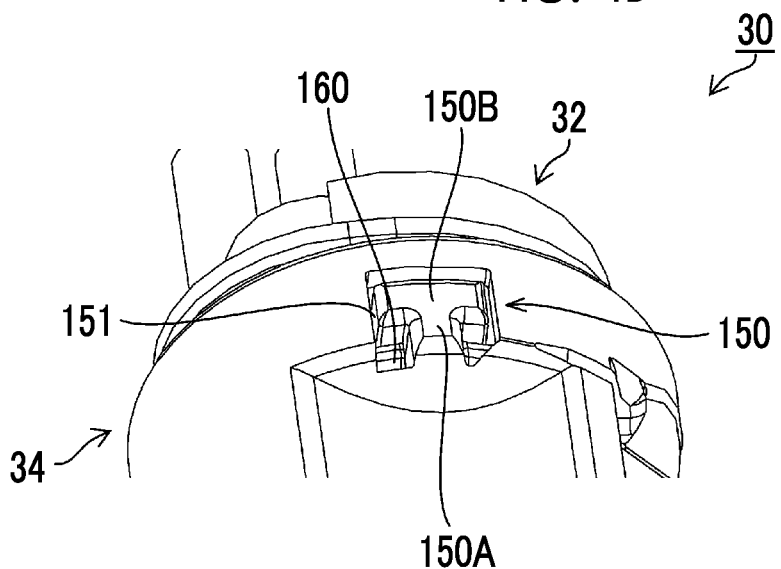
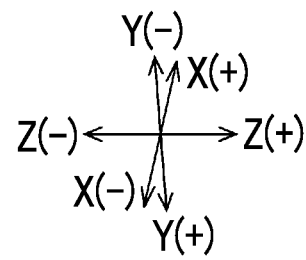

FIG. 5
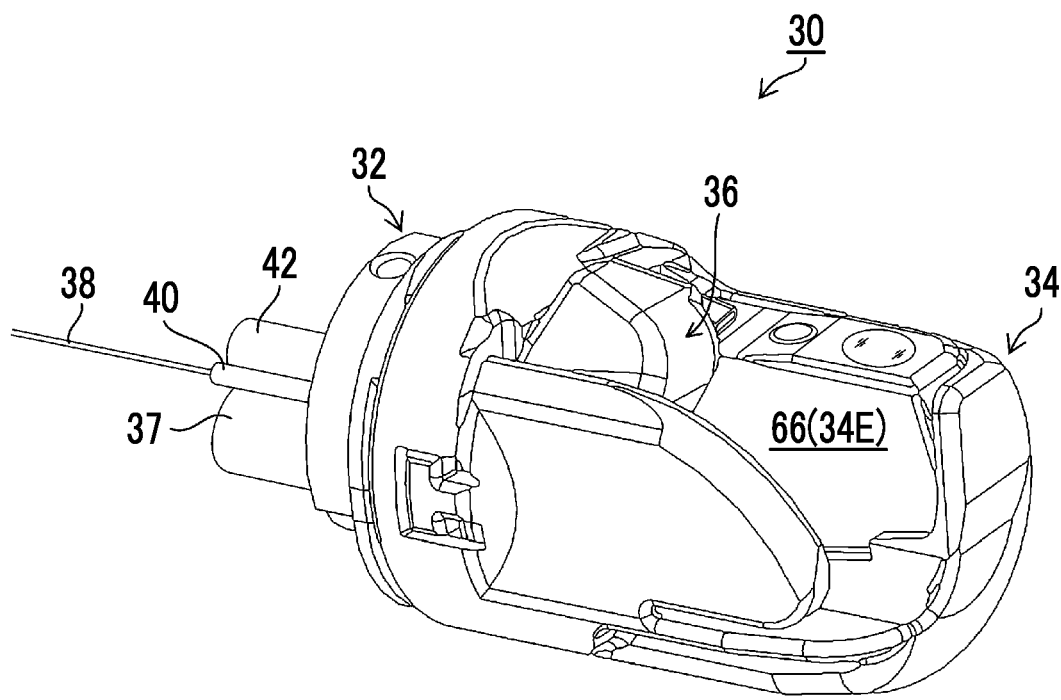
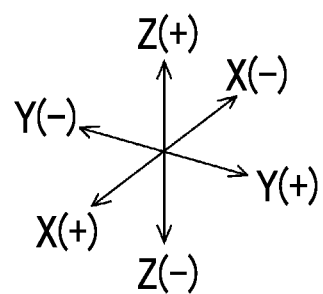

FIG. 6
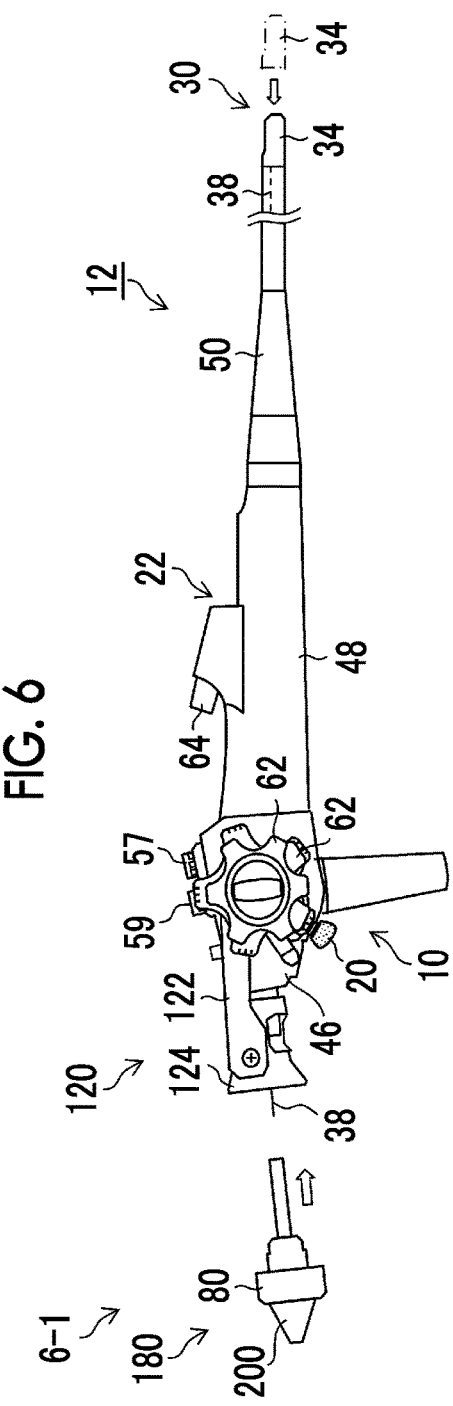
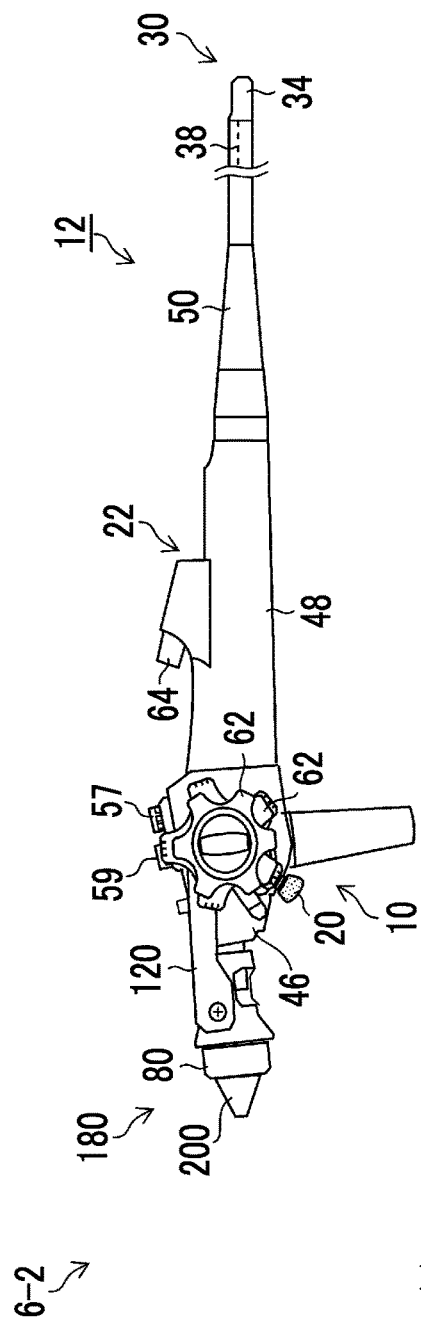
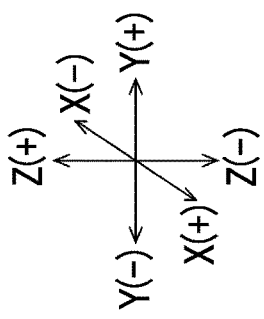

FIG. 11
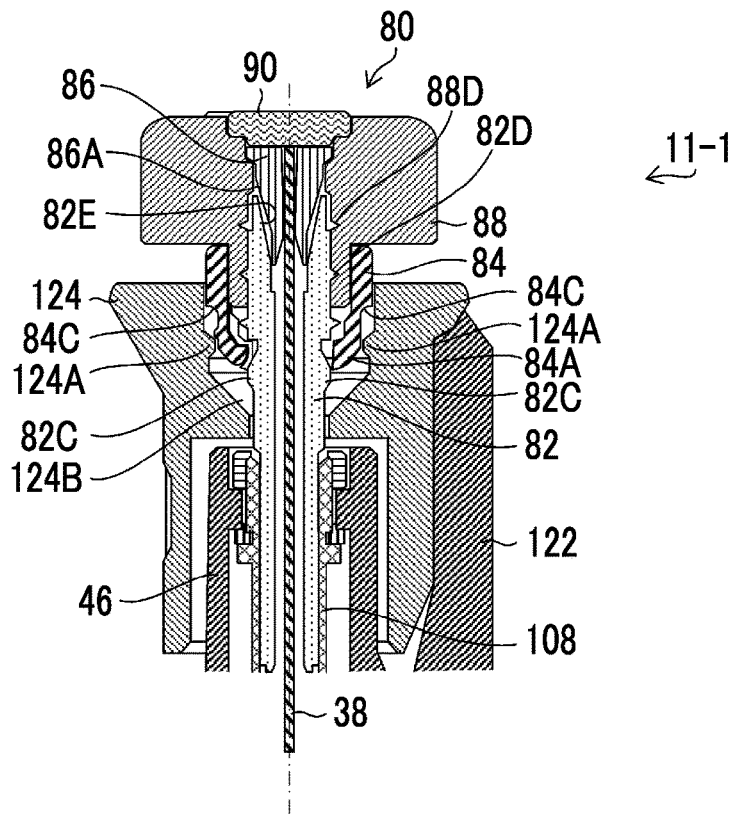
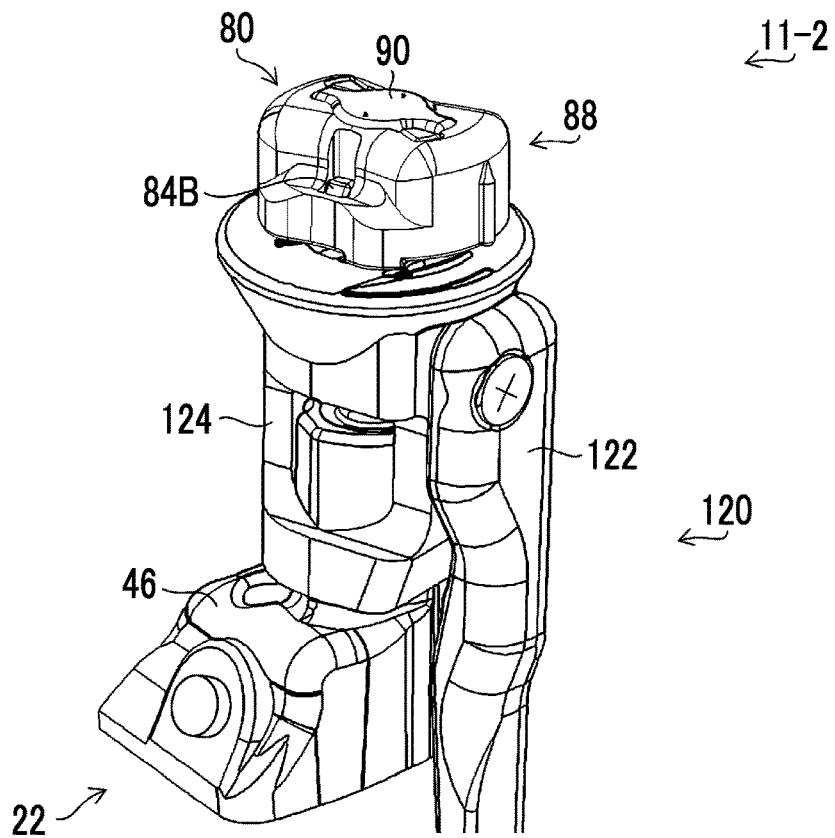

FIG. 12
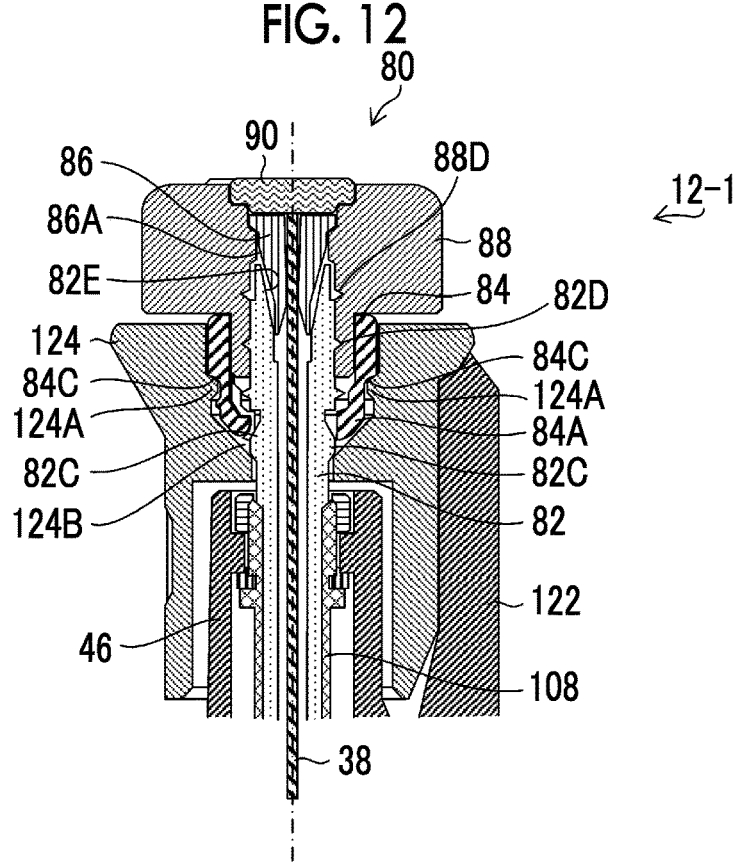
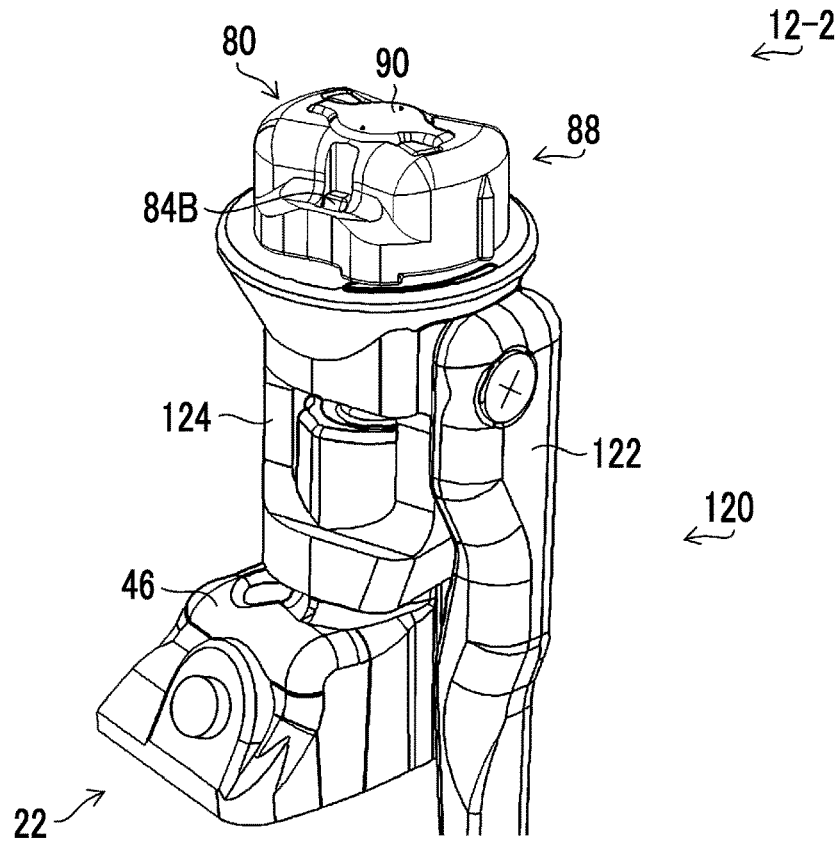

FIG. 13
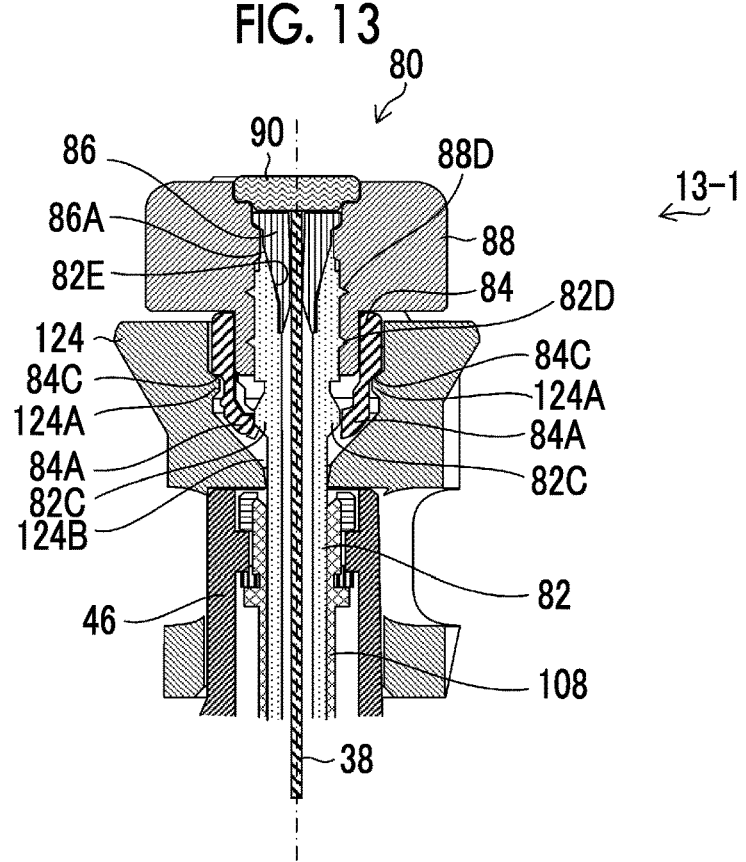
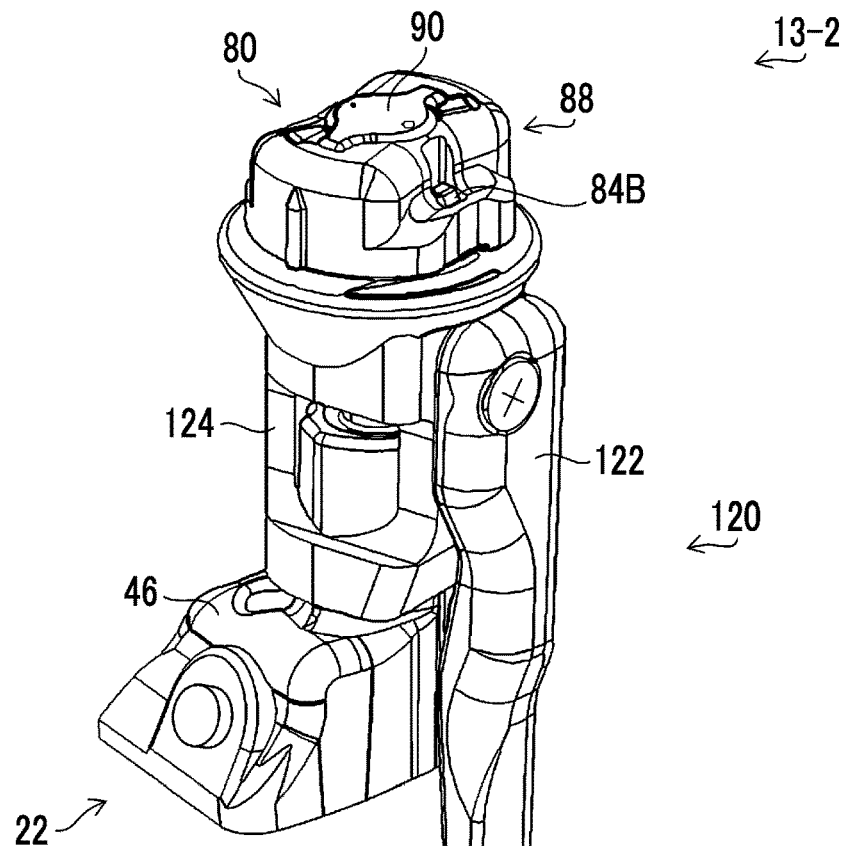

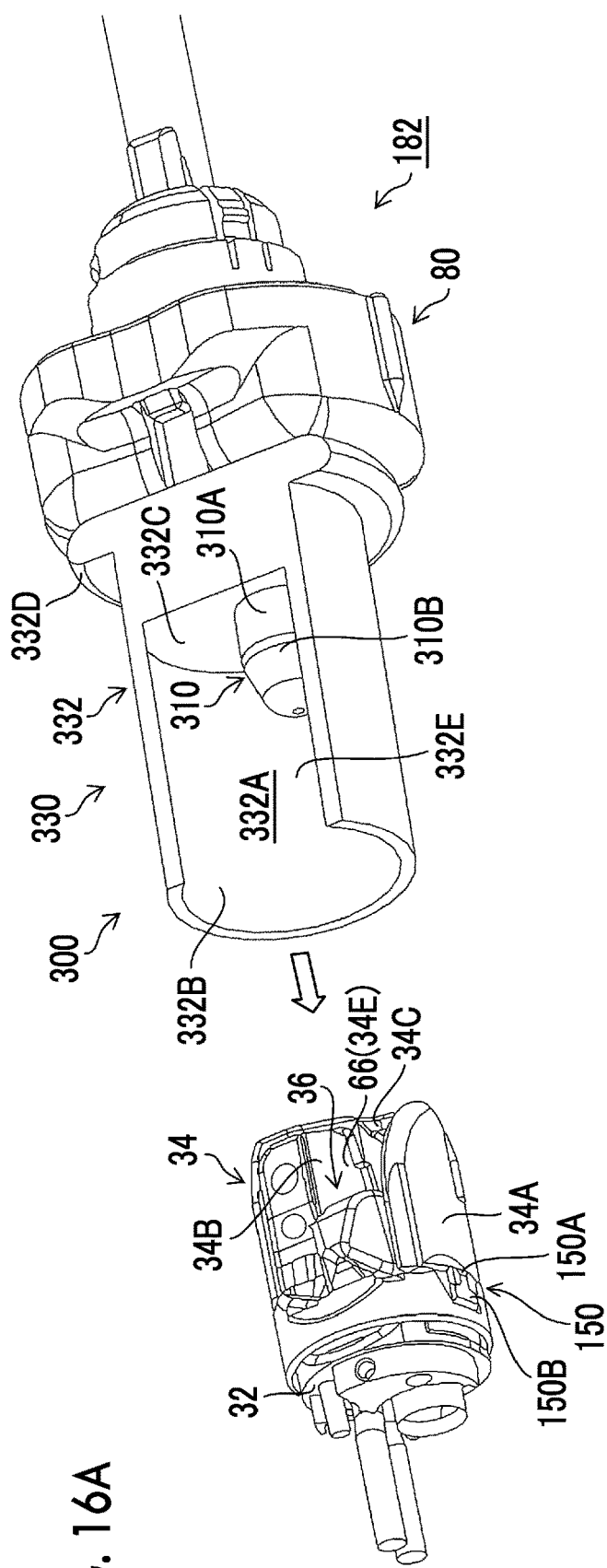
FIG. 16A
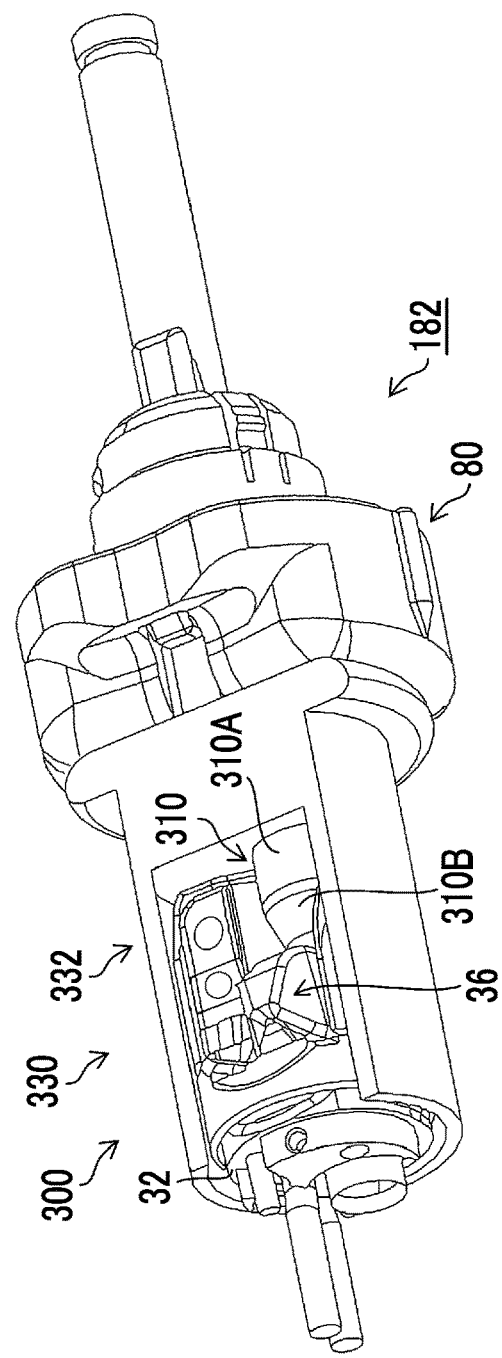
FIG. 16B
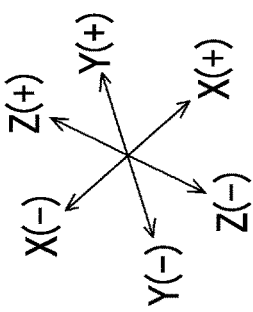

ENDOSCOPE AND MOUNTING COMPONENT

CROSS-REFERENCE TO RELATED APPLICATION

The present application claims priority under 35 U.S.C. § 119(a) to Japanese Patent Application No. 2020-142537 filed on Aug. 26, 2020, which is hereby expressly incorporated by reference, in its entirety, into the present application.

BACKGROUND OF THE INVENTION

1. Field of the Invention

The present invention relates to an endoscope and a mounting component.

2. Description of the Related Art

In the endoscope, various treatment tools are introduced from the treatment tool inlet port provided in the operation part, and the treatment tools are led out of the treatment tool outlet port opened to the distal end of the insertion part to be used for treatment. For example, a treatment tool such as a guide wire or a contrast tube is used in a duodenal endoscope. A treatment tool such as a puncture needle is used in ultrasonic endoscope. A treatment tool such as forceps or a snare is used in other forward-viewing endoscopes and oblique-viewing endoscopes. In order to perform treatment at a desired position in an object to be examined, the lead-out direction of such a treatment tool needs to be changed at a distal end thereof. For this purpose, a distal-end-portion body of the distal end portion is provided with an elevator that changes the lead-out direction of the treatment tool. The endoscope is provided with a treatment-tool elevating mechanism that changes the posture of the elevator between an elevating position and a lying position.

The endoscope needs to be washed after the treatment. Therefore, a distal end cap is attachably and detachably mounted on the distal-end-portion body provided with the elevator, and the distal end cap is detached by using a jig after the treatment, so that washability is improved.

In JP1995-265257A (JP-H07-265257A), in order to detach the distal end cap from the distal-end-portion body, a detachment jig that is engaged with the distal end cap is provided in a protruding manner on the outer surface of a rigid portion other than the insertion part of the endoscope.

SUMMARY OF THE INVENTION

Incidentally, there is a concern that a heavy load may be applied to the distal end portion in a case where the attachment/detachment procedure is incorrect when the distal end cap is detached by using the detachment jig.

The present invention has been made in view of such circumstances, and an object thereof is to provide an endoscope and a mounting component which are capable of safely detaching the distal end cap from the distal-end-portion body.

An endoscope according to a first aspect comprises: an operation part that is provided with an operation member; an insertion part that is provided on a distal end side of the operation part and is inserted into an object to be examined; an elevator that is provided in a distal end portion of the insertion part; a distal end cap that is mounted on the distal end portion and has an inner space communicating with a cap opening; an elevating operation wire of which a distal end side is connected to the elevator and which is pushed and pulled in response to operation of the operation member to operate the elevator; a wire channel through which the elevating operation wire is inserted; and a mounting component that is attachably and detachably mounted on the operation part, in which the mounting component has a wire fixing section that mechanically connects the operation member and the elevating operation wire to each other, and a jig section capable of detaching the distal end cap from the distal end portion.

In the endoscope according to a second aspect, the jig section includes a body portion having an inclined surface, the inclined surface is tapered in a direction of insertion into the inner space of the distal end cap, and in a case where the body portion is inserted into the inner space of the distal end cap, the inclined surface deforms the distal end cap in a direction of expanding the inner space of the distal end cap.

In the endoscope according to a third aspect, the jig section includes a connection portion that is connected to the body portion, the connection portion has a housing member in which a space that houses the distal end cap is formed, the housing member has a first opening that allows housing the distal end cap and a bottom that faces the first opening, and the body portion is connected to the bottom at a position opposite to the direction of insertion of the body portion.

In the endoscope according to a fourth aspect, the jig section has two wall members that are spaced apart and arranged to face each other, a part of the distal end cap is inserted between the two wall members with one of the wall members inserted into the inner space of the distal end cap, and the jig section deforms the distal end cap in a direction of expanding the inner space of the distal end cap with a force applied to the part of the distal end cap by rotation of the jig section around an axis of a major axis direction of the insertion part.

A mounting component according to a fifth aspect that is attachably and detachably mounted on an operation part of an endoscope, the mounting component comprises: a wire fixing section; and a jig section, in which the wire fixing section connects an elevating operation wire of which a distal end side is connected to an elevator provided in a distal end portion of an insertion part of the endoscope and an operation member provided in the operation part to each other, and the jig section is a section that is used to detach a distal end cap mounted on a distal end portion of the endoscope and having an inner space communicating with a cap opening, from the distal end portion.

In the mounting component according to a sixth aspect, the jig section includes a body portion having an inclined surface, the inclined surface is tapered in a direction of insertion into the inner space of the distal end cap, and in a case where the body portion is inserted into the inner space of the distal end cap, the inclined surface deforms the distal end cap in a direction of expanding the inner space of the distal end cap.

In the mounting component according to a seventh aspect, the jig section includes a connection portion that is connected to the body portion, the connection portion has a housing member in which a space that houses the distal end cap is formed,
the housing member has a first opening that allows housing the distal end cap and a bottom that faces the first opening, and the body portion is connected to the bottom at a position opposite to the direction of insertion of the body portion.

In the mounting component according to an eighth aspect, the jig section has two wall members that are spaced apart and arranged to face each other, a part of the distal end cap is inserted between the two wall members with one of the wall members inserted into the inner space of the distal end cap, and the jig section deforms the distal end cap in a direction of expanding the inner space of the distal end cap with a force applied to the part of the distal end cap by rotation of the jig section around an axis of a major axis direction of the insertion part.

With the endoscope and the mounting component according to the aspects of the present invention, the distal end cap can be safely detached from the distal-end-portion body.

BRIEF DESCRIPTION OF THE DRAWINGS

FIGS. 4A and 4B are enlarged perspective views of the distal end portion.

FIG. 5 is a perspective view of the distal end portion when viewed from an angle different from that of FIG. 2.

FIG. 6 is a diagram showing a procedure for fixing a wire using a first embodiment of a mounting component.

FIG. 11 is a diagram showing the procedure for fixing the elevating operation wire and the link member using the wire fixing section of the mounting component of the first embodiment.

FIG. 12 is a diagram showing the procedure for fixing the elevating operation wire and the link member using the wire fixing section of the mounting component of the first embodiment.

FIG. 13 is a diagram showing the procedure for fixing the elevating operation wire and the link member using the wire fixing section of the mounting component of the first embodiment.

FIGS. 16A and 16B are diagrams showing a procedure for detaching the distal end cap using the second embodiment of the mounting component.

DESCRIPTION OF THE PREFERRED EMBODIMENTS

First Embodiment

Figure 1:
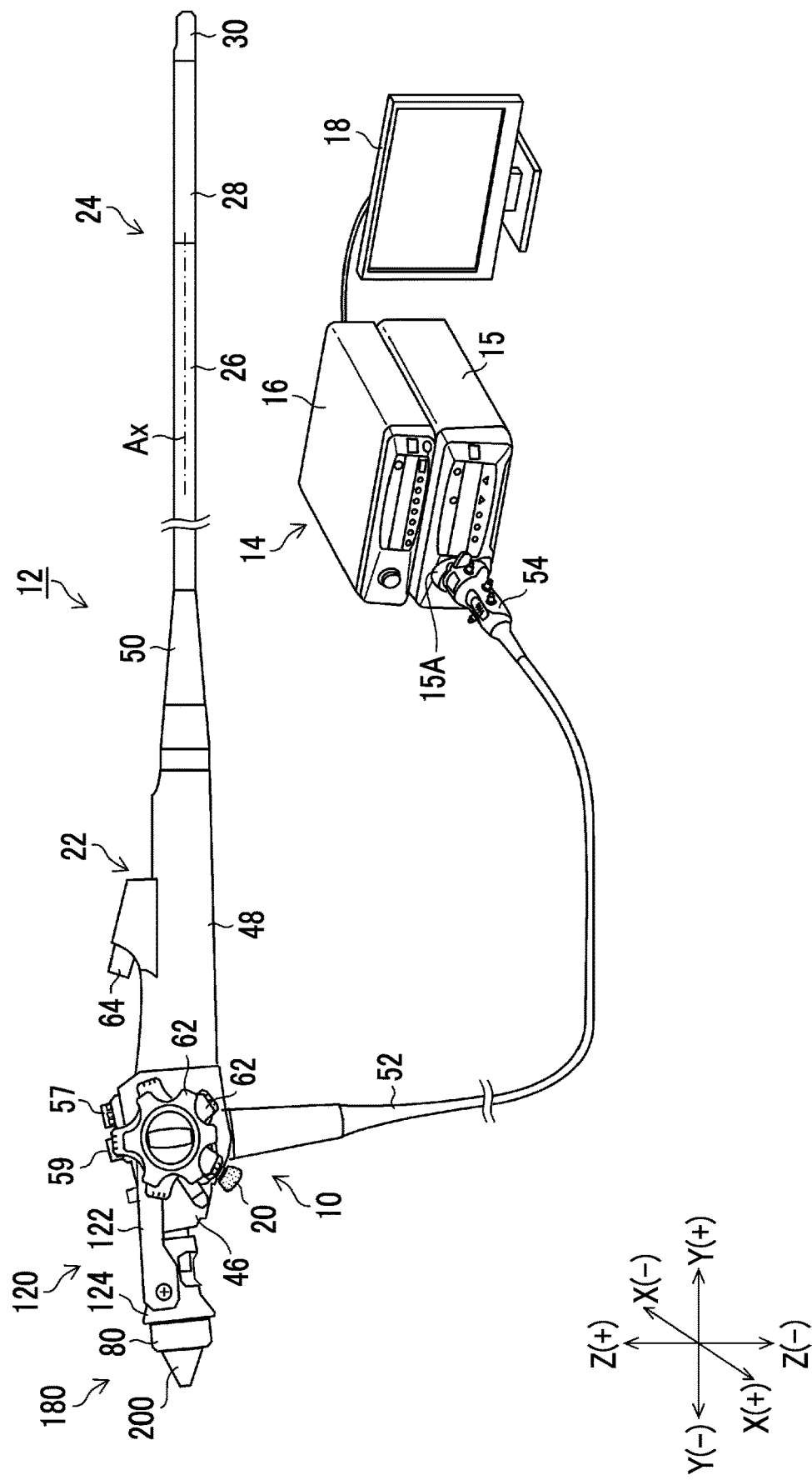
FIG. 1 is a diagram showing a configuration of an endoscope system including an endoscope.

FIG. 1 is a diagram showing a configuration of an endoscope system 12 including an endoscope 10. The endoscope system 12 comprises the endoscope 10, an endoscope processor apparatus 14, and a display 18.

The endoscope 10 comprises a proximal operation part 22 (also referred to as an operation part) provided with an elevating operation lever 20, and an insertion part 24 of which the proximal end is connected to the proximal operation part 22 and which is inserted into an object to be examined. The elevating operation lever 20 is an example of an operation member.

The insertion part 24 has a major axis direction Ax from the proximal end to the distal end, and comprises a soft portion 26, a bendable portion 28, and a distal end portion 30 in this order from the proximal end side to the distal end side. The schematic configuration of the distal end portion 30 will be described.

Figure 2:
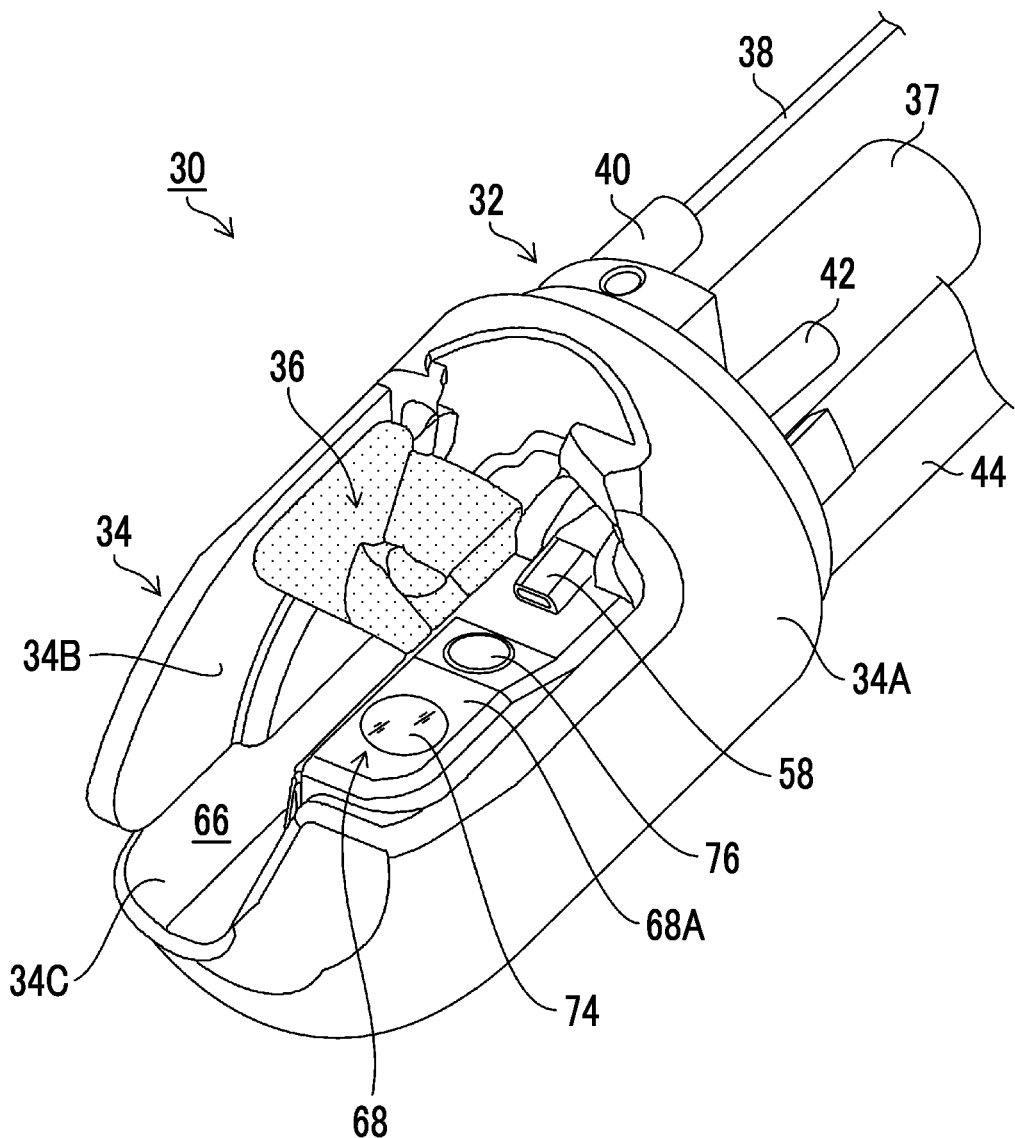
FIG. 2 is a perspective view of a distal end portion.

FIG. 2 is an enlarged perspective view of the distal end portion 30. Here, the endoscope 10 (see FIG. 1) is a side-viewing endoscope (also referred to as a side-viewing scope) that is used as, for example, a duodenal endoscope, and the distal end portion 30 of FIG. 2 has a configuration of a side-viewing endoscope.

In FIG. 2, a distal end cap 34 is mounted on the distal-end-portion body 32, whereby the distal end portion 30 is formed. A treatment tool elevator 36 (hereinafter, elevator 36) is attached to the distal end cap 34.

FIG. 2 shows various components provided in the insertion part 24 of the endoscope 10 (see FIG. 1), in addition to the distal end portion 30. A treatment tool channel 37 that guides the distal end of a treatment tool (not shown) to the distal-end-portion body 32, an elevating operation wire 38 (hereinafter, referred to as a wire 38) that is used to perform operation for changing the lead-out direction of the distal end of the treatment tool led out of the distal-end-portion body 32, a wire channel 40 through which the wire 38 is inserted, an air/water supply tube 42, and a cable insertion channel 44 are shown. An air/water supply nozzle 58 is connected to the air/water supply tube 42 and communicates with the air/water supply tube 42. Further, components such as a light guide (not shown) that guides illumination light supplied from a light source device 15 (see FIG. 1) to the distal-end-portion body 32 and an angle wire (not shown) that is used to perform operation for bending the bendable portion 28 (see FIG. 1) are provided in the insertion part 24. The wire 38 is inserted through the wire channel 40 and disposed therein so as to be able to advance and retreat. The wire channel 40 is disposed from the proximal operation part 22 (see FIG. 1) to the insertion part 24. An illumination window 74 that is used to emit light and an observation window 76 that is used to capture an observation image are provided on the front end face of the distal end portion 30.

In the present specification, a three-dimensional Cartesian coordinate system including three-axis directions (an X-axis direction, a Y-axis direction, and a Z-axis direction) will be used to make a description. That is, in a case where the lead-out direction of the treatment tool (not shown) by the elevator 36 when the distal end portion 30 is viewed from the proximal operation part 22 is set as an upward direction, the upward direction indicates a Z(+) direction and a downward direction which is a direction opposite to the upward direction indicates a Z(−) direction. Further, in this case, a right direction indicates an X(+) direction and a left direction indicates an X(−) direction. Furthermore, in this case, a forward direction (a direction toward the distal end in the major axis direction Ax of the insertion part 24) indicates a Y(+) direction and a rearward direction (a direction toward the proximal end in the major axis direction Ax of the insertion part 24) indicates a Y(−) direction. The Y-axis direction including the Y(+) direction and the Y(−) direction is a direction parallel to the major axis direction Ax of the insertion part 24. The Z-axis direction is a direction orthogonal to the major axis direction Ax. The X-axis direction is a direction orthogonal to each of the Y-axis direction and the Z-axis direction.

As shown in FIG. 1, the proximal operation part 22 is formed in a substantially cylindrical shape as a whole. The proximal operation part 22 has an operation-part body 46 provided with the elevating operation lever 20 and a grip portion 48 linked to the operation-part body 46. The grip portion 48 is a portion that is gripped by the operator when the endoscope 10 is operated, and the proximal end of the insertion part 24 is connected to the distal end side of the grip portion 48 through a bending-proof pipe 50. A link member 120 is disposed outside the operation-part body 46. The link member 120 moves in conjunction with the operation of the elevating operation lever 20. The link member 120 comprises a rod 122 and a connection member 124. The distal end side of the rod 122 is connected to the elevating operation lever 20.

A mounting component 180 is attachably and detachably mounted on the proximal end side of the proximal operation part 22. The mounting component 180 includes a wire fixing section 80 and a jig section 200. The wire fixing section 80 and the jig section 200 are connected to each other in an inseparable state in normal use.

The wire fixing section 80 of the mounting component 180 is housed and fixed in the connection member 124 on the proximal end side of the link member 120. The wire fixing section 80 fixes the wire 38 (see FIG. 6). The wire fixing section 80 fixes the wire 38 and the link member 120. The elevating operation lever 20 and the wire 38 are mechanically connected by the wire fixing section 80 and the link member 120. Further, the jig section 200 facilitates detachment of the distal end cap 34 from the distal end portion 30, as will be described later.

In the mounting component 180 according to the embodiment, the wire fixing section 80 has a function of fixing the wire 38, and the jig section 200 has a function of detaching the distal end cap 34. Since the wire fixing section 80 and the jig section 200 are inseparable from each other, the states in which the mounting component 180 exerts the functions of the wire fixing section 80 and the jig section 200 are different from each other. The wire fixing section 80 may exert the function thereof when the mounting component 180 is attached to the proximal operation part 22, and the jig section 200 may exert the function thereof when the mounting component 180 is detached from the proximal operation part 22. That is, the mounting component 180 has a configuration in which the wire fixing section 80 and the jig section 200 cannot simultaneously exert their functions.

The proximal end of a universal cable 52 is connected to the operation-part body 46, and a connector device 54 is provided in the distal end of the universal cable 52. The connector device 54 is connected to an endoscope processor apparatus 14. The endoscope processor apparatus 14 comprises a light source device 15 and an image processing device 16. The light source device 15 is provided with a processor-side connector 15A to which the connector device 54 is connected. Further, the display 18 that displays an image which is subjected to image processing by the image processing device 16 is connected to the image processing device 16. The endoscope system 12 has a configuration in which power, optical signals, and the like are transmitted between the endoscope 10 and the endoscope processor apparatus 14 in a non-contact manner through a connector portion that is constituted of the connector device 54 and the processor-side connector 15A. Accordingly, the light from the light source device 15 is transmitted through an optical fiber cable (not shown) and is emitted from the illumination window 74 (see FIG. 2) provided on the front end face of the distal end portion 30. Further, the optical signal of the image captured from the observation window 76 (see FIG. 2) is subjected to image processing by the image processing device 16 and is displayed as an image on the display 18.

Further, an air/water supply button 57 and a suction button 59 are arranged side by side on the operation-part body 46. The air/water supply button 57 is a button that can be operated in two stages, and air may be supplied to the air/water supply nozzle 58 (see FIG. 2) through the air/water supply tube 42 by the first-stage operation, and water may be supplied to the air/water supply nozzle 58 through the air/water supply tube 42 by the second-stage operation. Further, in a case where the suction button 59 is operated, body fluid, such as blood, may be sucked from the treatment tool outlet port 60 (see FIG. 3) through the treatment tool channel 37.

As shown in FIG. 1, a pair of angle knobs 62 and 62 that are used to perform operation for bending the bendable portion 28 are arranged on the operation-part body 46. The pair of angle knobs 62 and 62 are coaxially provided so as to be rotationally movable. For example, four angle wires (not shown) are connected to the angle knobs 62 and 62, and the bendable portion 28, and the angle wires are pushed and pulled by the rotationally moving operation of the angle knobs 62 and 62, so that the bendable portion 28 is vertically and laterally bent.

Further, the elevating operation lever 20 is rotatably provided coaxially with the angle knobs 62 and 62. The elevating operation lever 20 is rotationally operated by the hand of the operator who grips the grip portion 48. In a case where the elevating operation lever 20 is rotationally operated, the link member 120 moves, and the wire fixing section 80 fixed to the link member 120 moves. Since the wire 38 shown in FIG. 2 is fixed to the wire fixing section 80, the wire 38 is pushed and pulled by this operation. The wire 38 is operated to be pushed and pulled, whereby the posture of the elevator 36 connected to the distal end of the wire 38 is changed between the lying position and the elevating position.

As shown in FIG. 1, the grip portion 48 of the proximal operation part 22 comprises a treatment tool inlet port 64 into which the treatment tool is introduced. The treatment tool (not shown) of which the distal end as a leading end is introduced from the treatment tool inlet port 64 is inserted through the treatment tool channel 37 (see FIG. 3) and is led out of the treatment tool outlet port 60 (see FIG. 3). Examples of the treatment tool may include treatment tools such as biopsy forceps of which the distal end has a cup capable of collecting body tissue, a knife for endoscopic sphincterotomy (EST), or a contrast tube.

Next, the structure of the distal end portion 30 will be described with reference to FIGS. 2 and 3. FIG. 2 is a perspective view of the distal end portion, and FIG. 3 is an exploded perspective view of the distal end portion.

Figure 3:
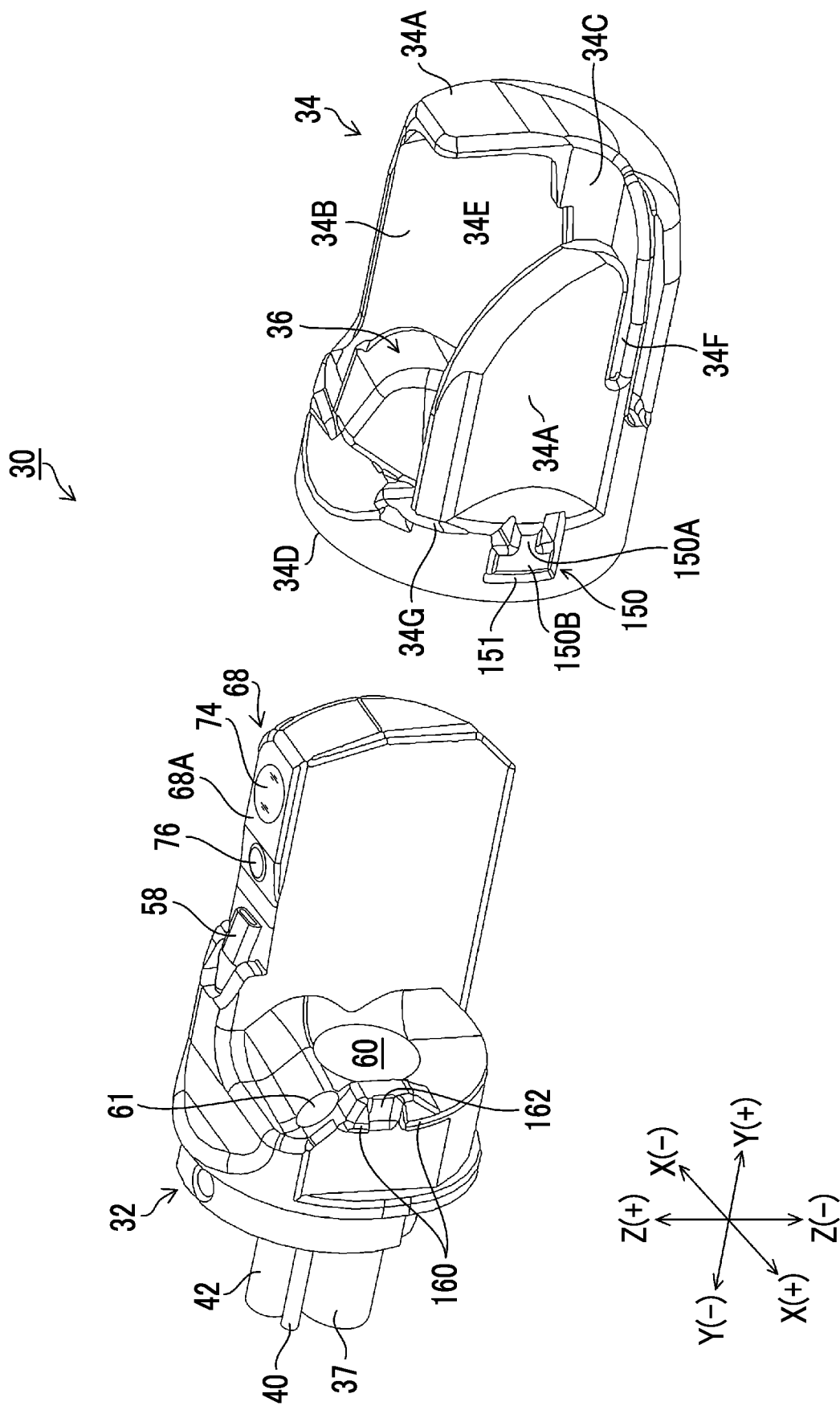
FIG. 3 is an exploded perspective view of the distal end portion.

The distal-end-portion body 32 is made of, for example, a metal material having corrosion resistance, and has a partition wall 68 provided in a protruding manner in the Y(+) direction as shown in FIGS. 2 and 3.

The illumination window 74 and an observation window 76 are arranged adjacent to each other in the Y-axis direction on the upper surface 68A on the Z(+) side of the partition wall 68. The illumination window 74 can irradiate the visual field region in the Z(+) direction with illumination light, and the observation window 76 can observe the visual field region in the Z(+) direction. The distal-end-portion body 32 is provided with the air/water supply nozzle 58 facing the observation window 76, and the observation window 76 is washed by air and water ejected from the air/water supply nozzle 58.

The distal end cap 34 shown in FIG. 2 or 3 is made of an elastic material, for example, a rubber material, such as fluororubber or silicone rubber, and a resin material, such as polysulfone or polycarbonate.

The distal end cap 34 comprises a cap opening 34B and a wall 34A that defines a distal end opening 34C continuous with the cap opening 34B. The wall 34A has a mounting opening 34D, and the mounting opening 34D allows the distal-end-portion body 32 to be inserted.

The distal end cap 34 is formed in a substantially tubular shape by the wall 34A that defines the cap opening 34B, the distal end opening 34C, and the mounting opening 34D, and an inner space 34E is formed in the distal end cap 34.

A through-hole 61 is formed in the distal-end-portion body 32, and the wire 38 (not shown) is inserted through the through-hole 61. The distal end of the wire 38 is connected to the elevator 36.

As shown in FIG. 2, when the distal end cap 34 is mounted on the distal-end-portion body 32, a part of the inner space 34E is occupied by the partition wall 68. The elevator housing space 66 is defined by the partition wall 68 and the wall 34A of the distal end cap 34. The elevator housing space 66 is disposed at a position on the X(+) direction side of the partition wall 68 and a position on the Y(+) direction side of the treatment tool outlet port 60.

As shown in FIG. 2, when the distal end cap 34 is mounted on the distal-end-portion body 32, the cap opening 34B is directed in the Z(+) direction. The treatment tool outlet port 60 (see FIG. 3) of the distal-end-portion body 32 communicates with the cap opening 34B through the elevator housing space 66.

The elevator 36 is rotatably supported in the inner space 34E of the distal end cap 34. A rotating shaft (not shown) is attached to the elevator 36. The rotating shaft is attached to the elevator 36 on the side opposite to the position facing the cap opening 34B. A bearing (not shown) that rotatably supports the rotating shaft of the elevator 36 is disposed in the inner space 34E of the distal end cap 34.

When the wire 38 shown in FIG. 2 is pushed and pulled, the elevator 36 is rotated about the rotating shaft, and the posture thereof is changed between the lying position and the elevating position.

The distal end cap 34 has a configuration in which the elevator 36 to which the wire 38 is connected is attached in advance. When the treatment using the endoscope 10 ends, the distal end cap 34 formed in this way is detached from the distal-end-portion body 32 as will be described later, and is discarded together with the elevator 36 and the wire 38 as, for example, a disposable member. The elevator 36 may be attached to the distal-end-portion body 32 instead of the distal end cap 34.

Next, mounting the distal end cap 34 on the distal-end-portion body 32 will be described with reference to FIGS. 3 to 5.

As shown in FIG. 3, the wall 34A of the distal end cap 34 faces the X(+) direction and the X(−) direction with the cap opening 34B interposed therebetween. The cantilever piece 150 is formed on the wall 34A opposite to the side where the partition wall 68 is inserted. A cutout 151 is provided in the distal end cap 34, whereby the cantilever piece 150 is formed. The cutout 151 penetrates the outside and the inside of the distal end cap 34.

The cantilever piece 150 comprises a support piece 150A and a stopped portion 150B connected to the support piece 150A. The side of the support piece 150A opposite to the stopped portion 150B is connected to the wall 34A to form a fixed end of the cantilever piece 150. The stopped portion 150B of the cantilever piece 150 is a free end that is not connected to the wall 34A. The cantilever piece 150 extends along the Y-axis direction, and the fixed end is positioned on the distal end side (Y(+) direction) than the free end.

The stopped portion 150B is larger in width in the Z-axis direction than the support piece 150A. When viewed in the X(+) direction, the cantilever piece 150 has a T-shape as a whole.

Since the support piece 150A is bent and deformed with the fixed end as a fulcrum, the stopped portion 150B, which is a free end, can be displaced in the X(+) direction and the X(−) direction.

As shown in FIG. 3, a first cut 34F and a second cut 34G are formed in the distal end cap 34. The first cut 34F is continuous with the distal end opening 34C and extends in the direction along the Y-axis direction. The first cut 34F penetrates the outside and the inside of the wall 34A of the distal end cap 34. The distal end cap 34 is divided into the Z(+) side and the Z(−) side with the first cut 34F as a boundary. The first cut 34F may not be completely parallel to the Y-axis direction as long as the first cut 34F extends along the Y-axis direction.

The second cut 34G extends in a direction orthogonal to the first cut 34F. The second cut 34G penetrates the outside and the inside of the wall 34A of the distal end cap 34. The second cut 34G is continuous with the cutout 151, extends in the Z(+) direction, and reaches the cap opening 34B. The distal end cap 34 is divided into the Y(+) side and the Y(−) side with the second cut 34G as a boundary. The first cut 34F and the second cut 34G have a positional relationship in which the first cut 34F and the second cut 34G are orthogonal to each other. Being orthogonal includes being completely orthogonal and being substantially orthogonal.

As shown in FIG. 3, the distal-end-portion body 32 has two stopper portions 160 on the side facing the cantilever piece 150. The two stopper portions 160 protrude in the X(+) direction. Further, the two stopper portions 160 are arranged along the Z-axis direction. A groove portion 162 is defined by the two stopper portions 160. The two stopper portions 160 are arranged at an interval that is narrower than the width of the stopped portion 150B and wider than the width of the support piece 150A.

FIGS. 4A and 4B are enlarged perspective views of the distal end portion 30, and FIG. 4A shows a state immediately before the distal end cap 34 is mounted on the distal-end-portion body 32 and FIG. 4B shows a state after the distal end cap 34 is mounted on the distal-end-portion body 32. When the distal end cap 34 is mounted on the distal-endportion body 32, the distal end cap 34 moves toward the distal-end-portion body 32 as shown in FIG. 4A.

As the distal end cap 34 moves, the stopped portion 150B of the cantilever piece 150 comes into contact with the two stopper portions 160. Further, when the distal end cap 34 moves toward the distal-end-portion body 32, the support piece 150A is bent and deformed in the X(+) direction with the fixed end as a fulcrum. The stopped portion 150B, which is a free end, moves in a direction of running on the two stopper portions 160.

As shown in FIG. 4B, when the distal end cap 34 moves to the mounting position with respect to the distal-end-portion body 32, the stopped portion 150B goes over the two stopper portions 160 and moves to the proximal end side (Y(−)) than the two stopper portions 160. The support piece 150A returns to the original state due to elastic deformation. As shown in FIG. 4A, since the interval between the two stopper portions 160 is narrower than the width of the stopped portion 150B, the two stopper portions 160 and the stopped portion 150B are engaged with each other. On the other hand, the support piece 150A is housed in the groove portion 162. The engagement between the stopper portions 160 and the stopped portion 150B prevents the distal end cap 34 from moving from the distal-end-portion body 32 in the Y(+) direction and falling out. As shown in FIG. 5, the distal end cap 34 is mounted on the distal-end-portion body 32.

FIG. 6 is a diagram illustrating a procedure for fixing the wire 38 using the mounting component 180. As shown in FIG. 6-1, when the distal end cap 34 is mounted on the distal-end-portion body 32 (see FIG. 5), the wire 38 protrudes from the connection member 124 of the link member 120 toward the proximal end side. The mounting component 180 is prepared and the wire fixing section 80 is positioned so as to face the wire 38. The wire fixing section 80 and the connection member 124 move in a direction of approaching each other.

As shown in FIG. 6-2, the wire 38 is housed in the wire fixing section 80. The wire fixing section 80 fixes the wire 38 and the link member 120. The wire fixing section 80 may comprise, for example, a collet. The collet has a plurality of gaps. The collet closes the gaps to grip and fix the wire 38. The collet opens the gaps to release the fixing of the wire 38. The opening and closing of the gaps of the collet may be linked to, for example, the rotational operation of the wire fixing section 80.

The wire 38 is fixed by the wire fixing section 80, whereby the mounting component 180 is attached to the proximal operation part 22. Preparation before treatment (examination) is completed, and the distal end portion 30 of the endoscope 10 may be inserted into the object to be examined. The treatment tool is directed in a desired lead-out direction in the object to be examined by the elevator 36 of the distal end portion 30. After the treatment (examination), the distal end cap 34 is detached by using the jig section 200 of the mounting component 180, and the distal end portion 30 is washed.

Hereinafter, the wire fixing section 80 and the jig section 200 of the mounting component 180 of a first embodiment will be described.

Figure 7:
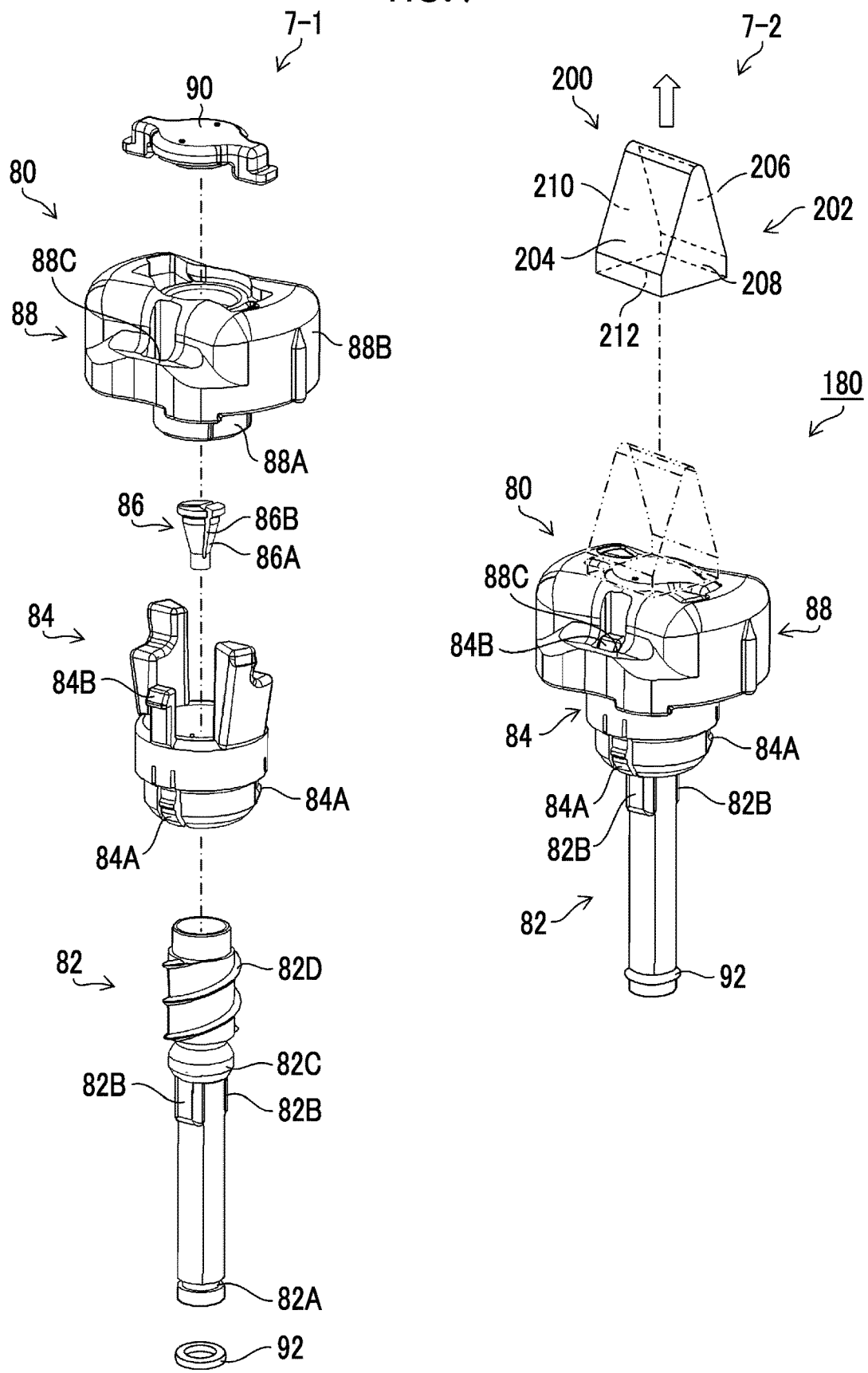
FIG. 7 is an assembly view of the first embodiment of the mounting component.

FIG. 7 is an exploded perspective view of the mounting component 180. In FIG. 7, the terms "distal end side" and "proximal end side" mean a positional relationship when the wire fixing section 80 of the mounting component 180 is attached to the proximal operation part 22 of the endoscope 10. In FIG. 7, the term "direction of insertion" means a direction in which the jig section 200 of the mounting component 180 faces the distal end cap 34 when the jig section 200 detaches the distal end cap 34.

As shown in FIG. 7-1, the wire fixing section 80 comprises a wire grip member 86, a sliding member 82 that houses the wire grip member 86, and holding members 84 and 88 that house the sliding member 82. A movement restriction member 90 that is used to restrict the movement of the wire grip member 86 is provided on the proximal end side of the holding member 88. The holding member 88 and the movement restriction member 90 are shown as separate members in FIG. 7, but may be formed of one member integrally molded.

The sliding member 82 is formed of a tubular member and has a through-hole penetrating from the proximal end side to the distal end side. A groove 82A is formed on the outer peripheral surface of the sliding member 82 on the distal end side, and a packing 92 is disposed in the groove 82A. The packing 92 is, for example, an O-ring.

Two engaging portions 82B are formed on the outer peripheral surface of the sliding member 82 on the proximal end side than the groove 82A. The engaging portions 82B protrude radially outward of the sliding member 82 from the outer peripheral surface. The sliding member 82 comprises a snap restriction member 82C that protrudes along the outer peripheral surface, on the proximal end side than the engaging portions 82B. The sliding member 82 comprises a screw portion 82D on the proximal end side than the snap restriction member 82C. The screw portion 82D is formed in the shape of a male screw in which a screw thread protrudes from the outer peripheral surface.

The holding member 84 is formed of a two-stage tubular member and has a through-hole penetrating from the proximal end side to the distal end side. The outer shape of the holding member 84 on the distal end side is smaller in size than the outer shape thereof on the proximal end side. The holding member 84 comprises two snaps 84A. The snap 84A has a fixed end that is cantilevered on the proximal end side and a free end that extends to the distal end side. The snap 84A is elastically deformable with the fixed end as a fulcrum. The holding member 84 comprises a claw 84B extending from the proximal end side of the tubular member toward the proximal end side.

The wire grip member 86 has a tubular shape having a tapered surface, penetrates from the distal end side to the proximal end side, and has a through-hole through which the wire 38 (not shown) is inserted and which has a length in the major axis direction. The wire 38 may be inserted through the wire grip member 86. A plurality of slits 86B extending along the through-hole from the proximal end side to the distal end side are formed on the outer peripheral surface of the wire grip member 86. The wire grip member 86 is tightened to reduce the gaps of the plurality of slits 86B and reduce the diameter of the through-hole, so that the wire grip member 86 may fix the wire 38. The wire grip member 86 has a tapered surface 86A of which the diameter increases toward the proximal end side, on the outer peripheral surface. The wire grip member 86 is housed in the sliding member 82 from the proximal end side of the sliding member 82. The gaps of the slits 86B decrease when the sliding member 82 approaches the wire grip member 86, so that the diameter of the through-hole decreases. The gaps of the slits 86B increase to the original state when the sliding member 82 moves away from the wire grip member 86, so that the diameter of the through-hole increases. The wire fixing section 80 may attachably and detachably fix the wire 38 by the operation of reducing and enlarging the diameter of the through-hole of the wire grip member 86. A collet may be applied as an example of the wire grip member 86.

The holding member 88 is formed of a two-stage tubular member and has a through-hole penetrating from the proximal end side to the distal end side. The outer shape of the member 88A on the distal end side of the holding member 88 is smaller in size than the outer shape of the member 88B on the proximal end side. The member 88B has a substantially cylindrical shape and extends to the inside of the member 88A. The inner peripheral surface of the member 88B comprises a screw portion (not shown). The screw portion (not shown) is formed in the shape of a female screw having a screw thread on the inner peripheral surface of the member 88B. The member 88A of the holding member 88 is housed in the holding member 84.

The holding member 88 has an engagement surface 88C. The engagement surface 88C is formed on the member 88B and is engaged with the claw 84B of the holding member 84. The engagement surface 88C is formed of an opening edge of a through-hole formed in the member 88B. The through-hole of the member 88B extends from the distal end side to the proximal end side.

The movement restriction member 90 is disposed on the opening of the holding member 88 on the proximal end side. The movement restriction member 90 is formed in the shape of a thin plate having a thin thickness. Note that, the shape is not limited thereto. The operation of the wire fixing section 80 of the embodiment will be described later.

As shown in FIG. 7-2, the sliding member 82, the holding member 84, the wire grip member 86, the holding member 88, and the movement restriction member 90 are integrally assembled, whereby the wire fixing section 80 is formed. The screw portion 82D of the sliding member 82 and the screw portion 88D of the holding member 88 (see FIG. 11) movably mesh with each other.

In the present specification, the tubular shape is not limited to a cylindrical shape as long as the member has a through-hole, and may be formed in either a single-stage or multi-stage shape. The wire fixing section 80 is not limited to the structure as long as the wire fixing section 80 has a function of fixing the wire 38.

The jig section 200 comprises a body portion 202. The body portion 202 has two inclined surfaces 204 and 206 that face each other. The two inclined surfaces 204 and 206 are planes and are inclined with respect to the direction of insertion indicated by the arrow. The two inclined surfaces 204 and 206 intersect in the direction of insertion and form a tapered shape in the direction of insertion. The line of intersection between the inclined surfaces 204 and 206 extends in a straight line.

The body portion 202 comprises two planes 208 and 210 which face each other and connect the two inclined surfaces 204 and 206 to each other. The body portion 202 comprises a plane 212 on the side opposite to the direction of insertion. It is preferable that the body portion 202 is integrally molded. Since the body portion 202 of the jig section 200 deforms the distal end cap 34, the body portion 202 is preferably made of a material harder than the distal end cap 34. For example, the body portion 202 is made of a resin material, a metal material, or the like.

The plane 212 of the jig section 200 is connected to the holding member 88 and the movement restriction member 90 of the wire fixing section 80, and the wire fixing section 80 and the jig section 200 are formed to be inseparable in normal use.

Next, the procedure for detaching the distal end cap 34 using the jig section 200 of the mounting component 180 will be described.

It is required that the distal end cap 34 can be easily detached with a correct procedure from the distal-end-portion body 32 when the endoscope 10 is washed. As a correct procedure, it is important that the fixing of the wire 38 is released at least before the distal end cap 34 is detached. In a case where the fixing of the wire 38 is released, it is possible to avoid applying a heavy load to the bendable portion 28 having low rigidity when the distal end cap 34 is detached.

Further, in a case where the fixing of the wire 38 is released, it is not necessary to forcibly pull out the distal end cap 34.

Basically, the operation is performed in accordance with the reverse procedure of the procedure shown in FIG. 6. First, the fixing of the wire 38 on the proximal end side is released. For example, the wire fixing section 80 of the mounting component 180 is rotated, whereby the fixing between the wire fixing section 80 and the wire 38 is released. When the fixing of the wire 38 is released, the mounting component 180 can be detached from the proximal operation part 22.

Figure 8:
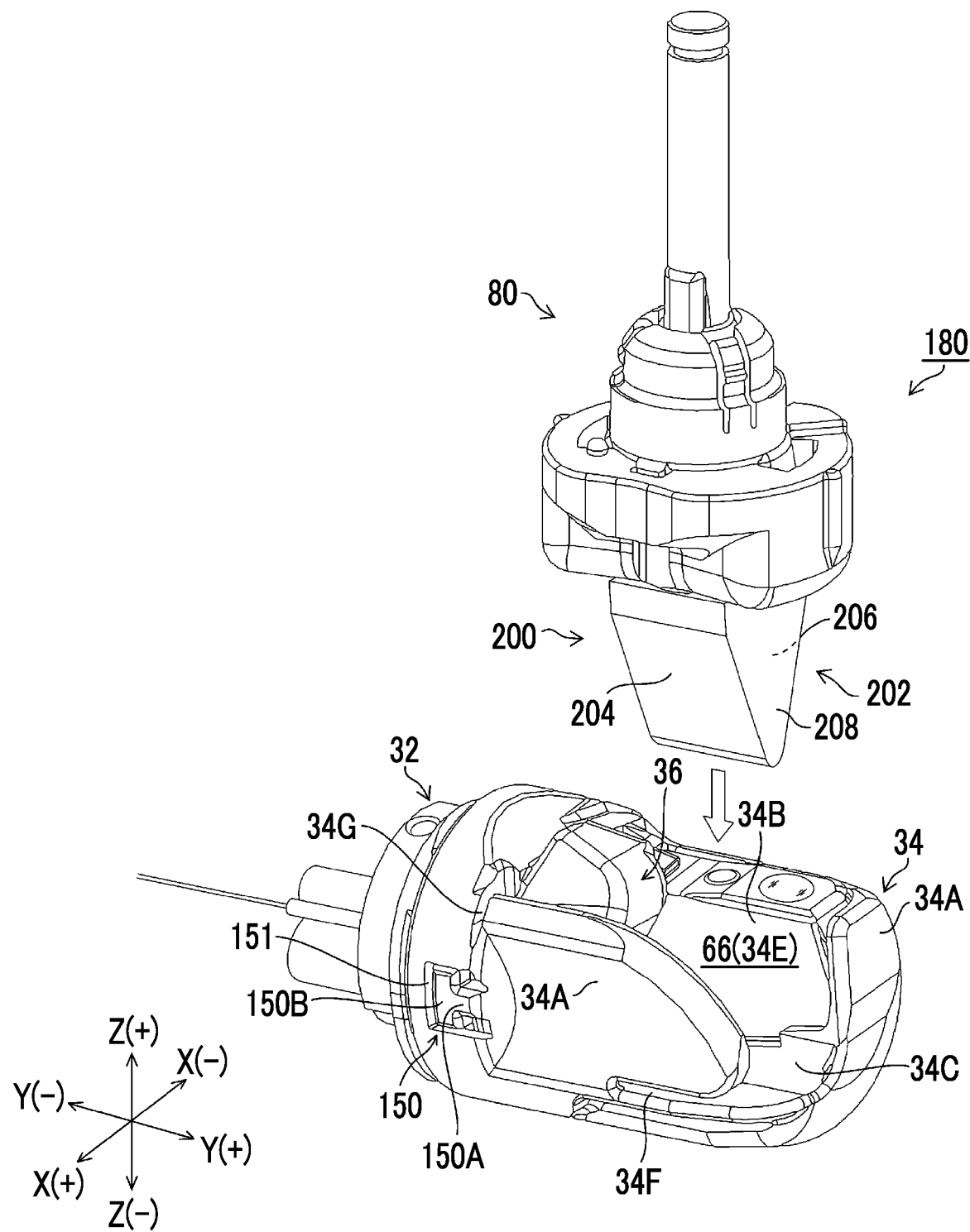
FIG. 8 is a diagram showing a procedure for detaching a distal end cap using a jig section of the mounting component of the first embodiment.
Figure 9:
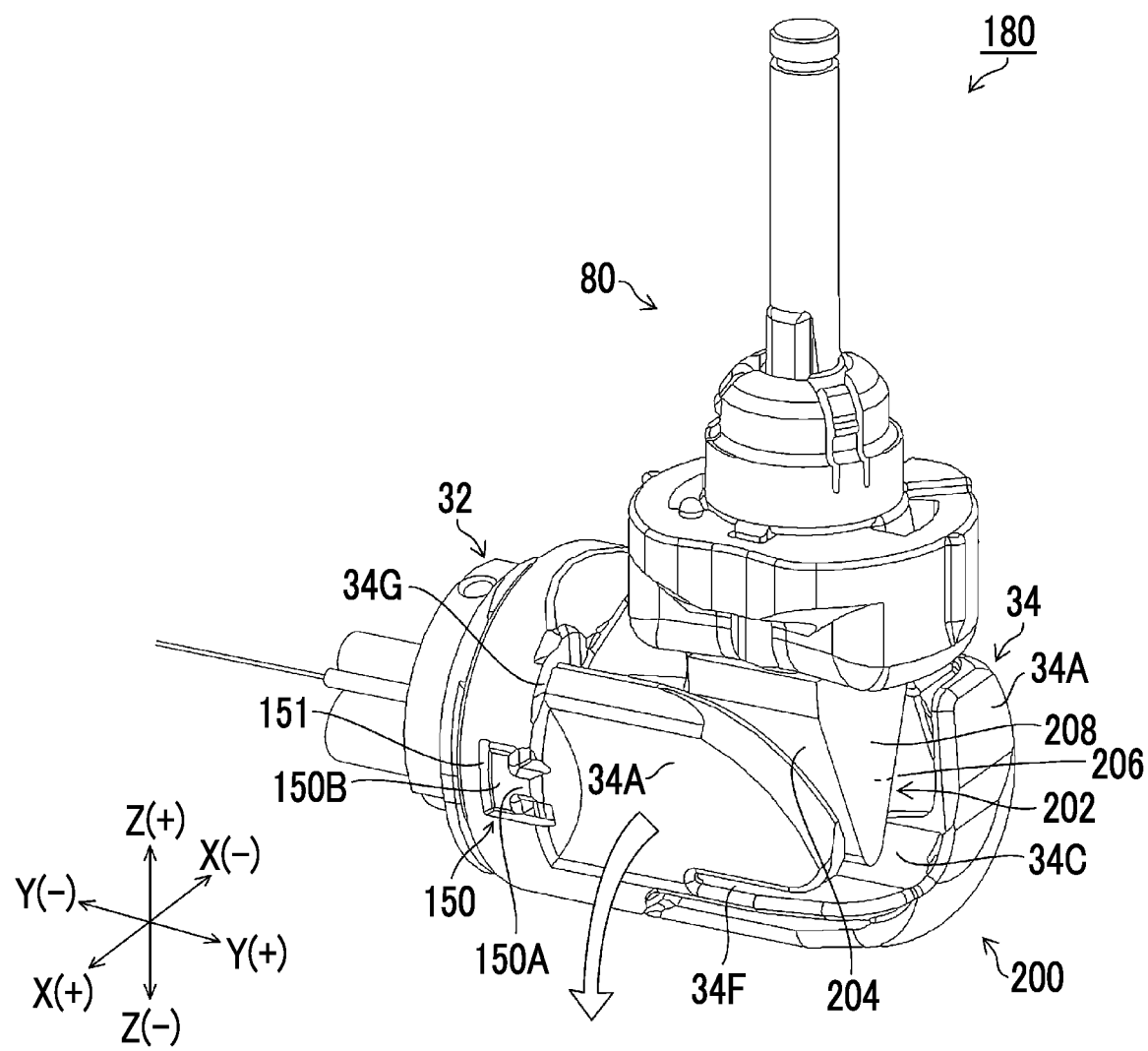
FIG. 9 is a diagram showing the procedure for detaching the distal end cap using the jig section of the mounting component of the first embodiment.

Next, a procedure for detaching the distal end cap 34 using the jig section 200 of the mounting component 180 will be described. FIGS. 8 and 9 are diagrams showing a procedure for detaching the distal end cap 34 using the first embodiment of the mounting component.

As shown in FIG. 8, the mounting component 180 detached from the proximal operation part 22 is prepared. The position of the jig section 200 of the mounting component 180 is adjusted with respect to the distal end cap 34 in a direction in which the tapered part of the body portion 202 faces the cap opening 34B and at least one inclined surface 204 comes into contact with the wall 34A. The line of intersection between the two inclined surfaces 204 and 206 is positioned in a direction substantially parallel to the Y-axis direction. When the distal end cap 34 is mounted on the distal-end-portion body 32, the elevator housing space 66 and the inner space 34E of the distal end cap 34 substantially coincide with each other.

In the mounting component 180 of the embodiment, the wire fixing section 80 and the jig section 200 are connected to each other. Therefore, in order to use the jig section 200, it is necessary to release the fixing between the wire fixing section 80 and the wire 38 and detach the mounting component 180 from the proximal operation part 22. As a result, the procedure for releasing the fixing of the wire 38 is carried out before the distal end cap 34 is detached.

As shown in FIG. 9, the body portion 202 is inserted into the inner space 34E of the distal end cap 34 through the cap opening 34B. For example, the wire fixing section 80 is grasped by a finger or the like, the mounting component 180 is pressed, and the body portion 202 is pushed into the inner space 34E of the distal end cap 34.

The distance between the inclined surfaces 204 and 206 increases in a direction opposite to the direction of insertion. The distance between the inclined surfaces 204 and 206 at a certain position is larger than the distance between the partition wall 68 and the wall 34A positioned on the X(+) side with respect to the partition wall 68.

As the body portion 202 is inserted into the inner space 34E of the distal end cap 34, the inclined surface 204 pushes the wall 34A in the direction (X(+) direction) of expanding the inner space 34E of the distal end cap 34, to deform the distal end cap 34. The deformation of the distal end cap 34 facilitates the detachment of the distal end cap 34 from the distal-end-portion body 32. A load applied to the bendable portion 28 (not shown) can be suppressed.

The deformation of the distal end cap 34 facilitates the release of the engaged stopped portion 150B and stopper portions 160.

Further, since the first cut 34F and the second cut 34G orthogonal to the first cut 34F are formed in the distal end cap 34, the wall 34A can be easily deformed.

The distal end cap 34 detached from the distal-end-portion body 32 is discarded without being reused.

Next, with reference to FIGS. 10 to 14, a procedure for fixing the wire 38 and the link member 120 using the wire fixing section 80 of the mounting component 180 will be described. In FIGS. 11 to 14, the jig section 200 is omitted.

First, the distal end cap 34 with the elevator 36 to which the wire 38 is connected is prepared (see FIG. 3). The wire 38 connected to the elevator 36 is inserted from the through-hole 61 of the distal-end-portion body 32 toward the proximal end side. The wire 38 is guided to the proximal end side of the proximal operation part 22 through the wire channel 40. The distal end cap 34 with the elevator 36 is mounted on the distal-end-portion body 32 (see FIG. 6).

Figure 10:
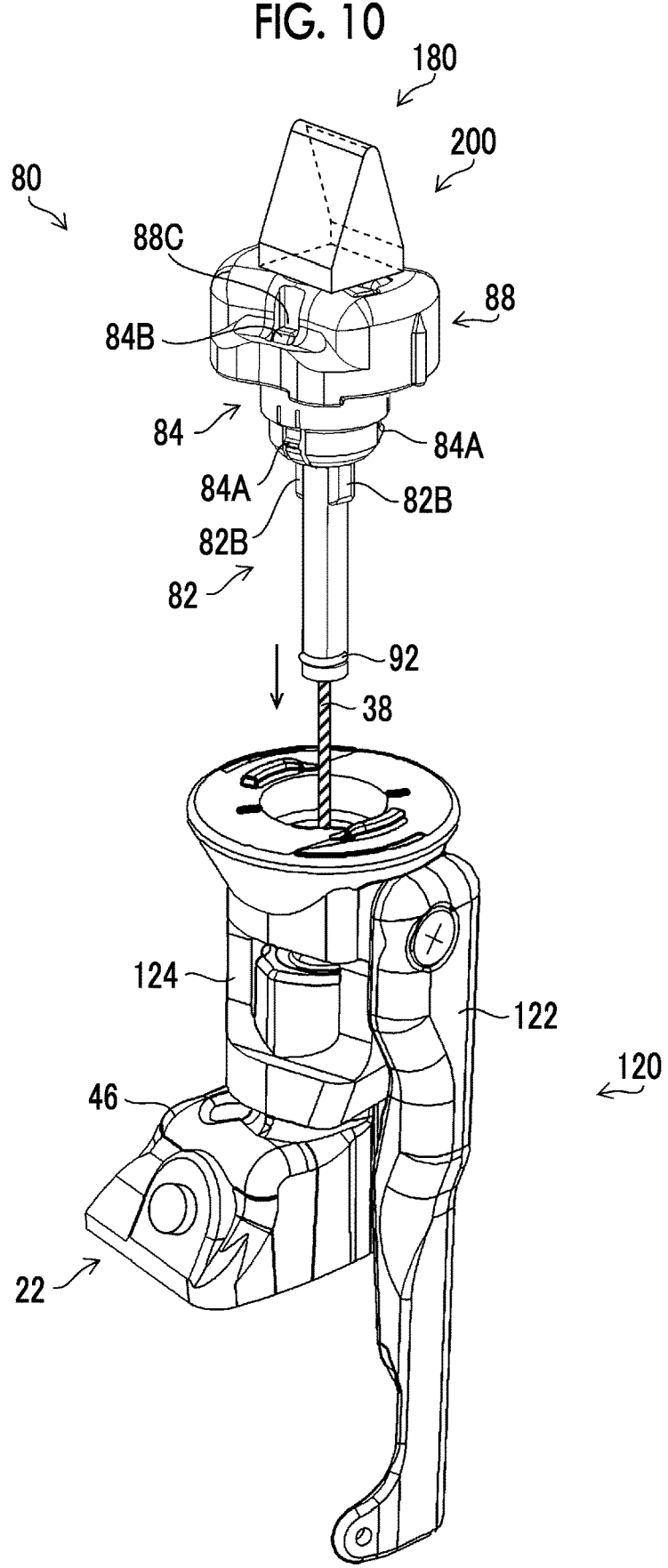
FIG. 10 is a diagram showing a procedure for fixing an elevating operation wire and a link member using a wire fixing section of the mounting component of the first embodiment.

As shown in FIG. 10, the wire 38 passes through the openings of the operation-part body 46 and the connection member 124 of the link member 120, and protrudes toward the proximal end side. The wire fixing section 80 is prepared and the sliding member 82 is positioned toward the opening of the connection member 124. The wire fixing section 80 and the connection member 124 move in a direction of approaching each other. The wire 38 is housed in the through-hole of the sliding member 82. In FIG. 10, the proximal end side of the wire 38 is housed in the through-hole of the sliding member 82.

FIG. 11 shows a state in which the wire fixing section 80 and the connection member 124 are closer to each other as compared with FIG. 10. As shown in FIG. 11-2, the wire fixing section 80 is substantially housed in the connection member 124 while the holding member 88 is left.

As shown in FIG. 11-1, the sliding member 82 of the wire fixing section 80 passes through the through-hole 124B of the connection member 124 and is guided to the sliding restriction pipe 108 of the operation-part body 46. A part of the sliding member 82 is housed in the connection member 124.

The protrusion 124A is continuously provided along the inner peripheral surface of the connection member 124. The protrusion 124A protrudes radially inward of the through-hole 124B of the connection member 124. The holding member 84 is housed in the connection member 124, and the snap 84A of the holding member 84 and the protrusion 124A come into contact with each other. The snap 84A is elastically deformed inward by the protrusion 124A with the fixed end as a fulcrum. A notch 84C housing the protrusion 124A is formed on the side closer to the fixed end of the snap 84A.

The inner peripheral surface of the through-hole 124B of the connection member 124 has a shape that follows the snap 84A on the distal end side than the protrusion 124A, and has a tapered shape toward the distal end side.

A tapered surface 82E is formed on the inner peripheral surface of the sliding member 82 on the proximal end side. The tapered surface 82E is disposed at a position spaced apart from the tapered surface 86A of the wire grip member 86 so as to face the tapered surface 86A.

A screw portion 88D that meshes with the screw portion 82D is provided on the inner peripheral surface of the through-hole of the holding member 88.

FIG. 12 shows a state in which the wire fixing section 80 and the connection member 124 are closer to each other as compared with FIG. 11. As shown in FIG. 12-2, the wire fixing section 80 is housed deeper in the connection member 124 while the holding member 88 is left.

As shown in FIG. 12-1, the wire fixing section 80 further moves to the distal end side, and the protrusion 124A is positioned at the notch 84C on the fixed end side of the snap 84A. In this state, the elastic deformation of the snap 84A is released, and the snap 84A returns to the shape of the natural body. The snap 84A is housed following the inner peripheral surface of the through-hole 124B.

The holding member 84 and the connection member 124 are snap-fit-engaged by the snap 84A and the protrusion 124A. The wire fixing section 80 and the connection member 124 are snapped into place, and the wire fixing section 80 and the connection member 124 are fixed by the snap-fit engagement.

FIG. 13 shows a state in which the wire fixing section 80 is rotated with respect to the connection member 124. As shown in FIG. 13-1, the wire fixing section 80 is rotated about ¼ clockwise with respect to the connection member 124 when viewed from the proximal end side.

As shown in FIG. 13-2, the connection member 124 restricts movement of the wire fixing section 80 to the distal end side.

In a case where the wire fixing section 80 is rotated, the holding member 84, the wire grip member 86, the holding member 88, and the movement restriction member 90, excluding the sliding member 82, are rotated. Since the screw portion 82D of the sliding member 82 and the screw portion 88D of the holding member 88 movably mesh with each other, the sliding member 82 moves to the proximal end side along the screw portion 88D of the holding member 88. On the other hand, the movement of the wire grip member 86 to the proximal end side is restricted by the movement restriction member 90. The sliding member 82 and the wire grip member 86 can move so as to approach each other, and the tapered surface 86A of the wire grip member 86 and the tapered surface 82E of the sliding member 82 come into contact with each other. The sliding member 82 tightens the wire grip member 86. With the tightening, the gaps of the slits 86B of the wire grip member 86 are reduced, the diameter of the through-hole is reduced, and the wire grip member 86 grips and fixes the wire 38.

The sliding member 82 moves to the proximal end side, whereby the snap restriction member 82C of the sliding member 82 is positioned in the free end of the snap 84A. Since the snap restriction member 82C fills the gap between the sliding member 82 and the snap 84A, the elastic deformation of the snap 84A is restricted. The restriction of the elastic deformation of the snap 84A prevents the wire fixing section 80 from falling out of the connection member 124.

Figure 14:
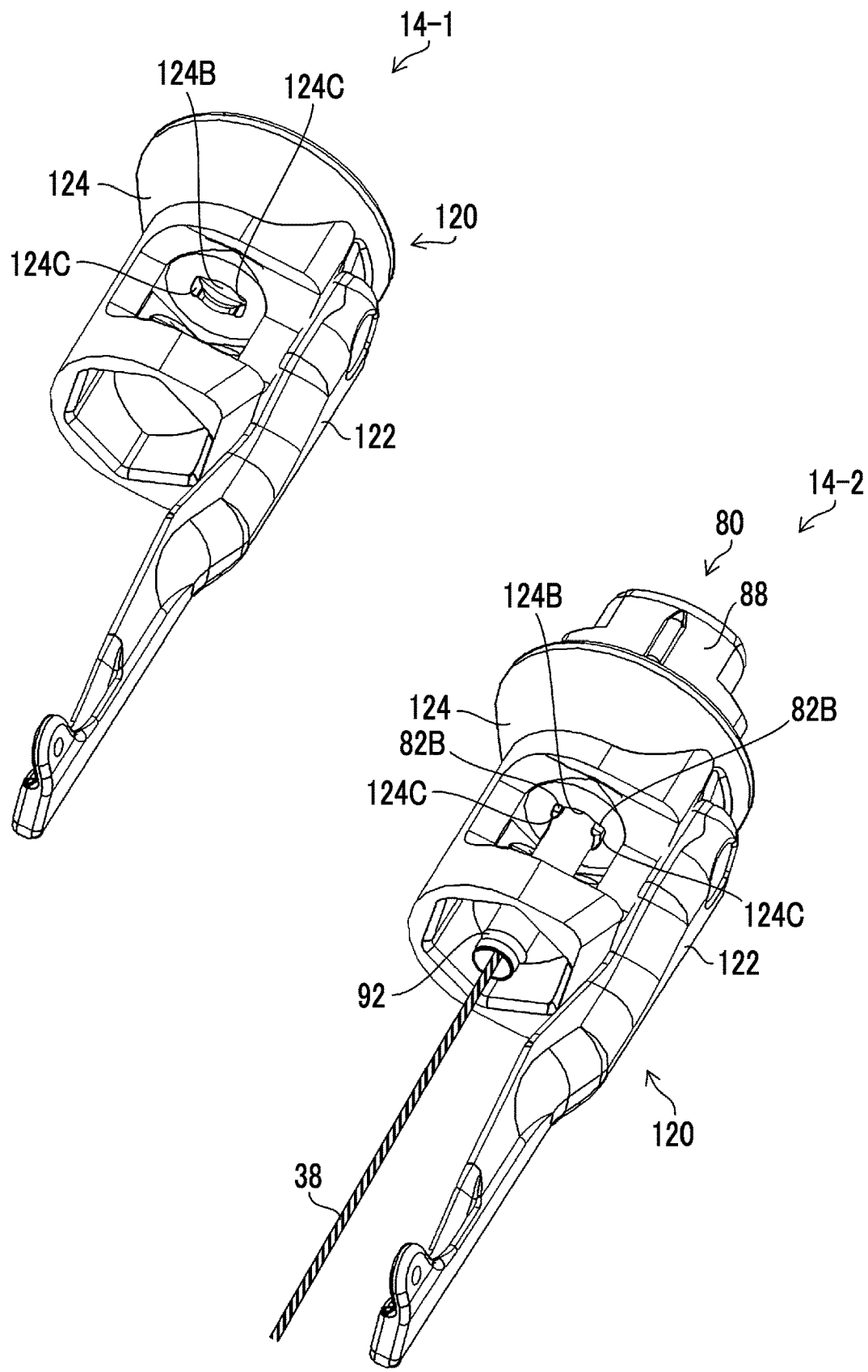
FIG. 14 is a diagram showing the procedure for fixing the elevating operation wire and the link member using the wire fixing section of the mounting component of the first embodiment.

Next, FIG. 14 is a perspective view of the link member 120 and the wire fixing section 80 when viewed from the distal end side. In FIG. 14-1, the wire fixing section 80 is omitted. As shown in FIG. 14-1, the through-hole 124B is formed in the connection member 124 of the link member 120. Engaged portions 124C are formed in the through-hole 124B. The engaged portion 124C is a so-called keyway formed along the through-hole 124B.

FIG. 14-2 shows a state after the wire fixing section 80 is rotated shown in FIG. 13. As shown in FIG. 14-2, the sliding member 82 of the wire fixing section 80 is inserted into the through-hole 124B of the connection member 124. Therefore, the sliding member 82 can move in the wire axial direction.

The engaging portions 82B of the sliding member 82 are engaged with the engaged portions 124C of the connection member 124. The engaging portion 82B and the engaged portion 124C are in a relationship of a key and a keyway. Since the sliding member 82 is engaged with the engaged portions 124C of the connection member 124, the rotation of the sliding member 82 is restricted. Alternatively, the engaging portion 82B may be used as a keyway, and the engaged portion 124C may be used as a key.

Since the rotation of the sliding member 82 is restricted, the sliding member 82 can move to the proximal end side with the screw portion 82D and the screw portion 88D meshing with each other when the holding members 84 and 88 of the wire fixing section 80 are rotated. As shown in FIGS. 10 to 14, the wire fixing section 80 of the embodiment is integrally formed, and the wire 38 and the link member 120 can be fixed by a simple operation.

In the embodiment, the holding members 84 and 88 of the wire fixing section 80 are rotated to tighten the wire grip member 86. The wire grip member 86 grips and fixes the wire 38 with the tightening.

Second Embodiment

A mounting component of a second embodiment will be described with reference to FIGS. 15 to 17. The same reference numerals may be given to the same configurations as those of the first embodiment, and the description thereof may be omitted.

Figure 15:
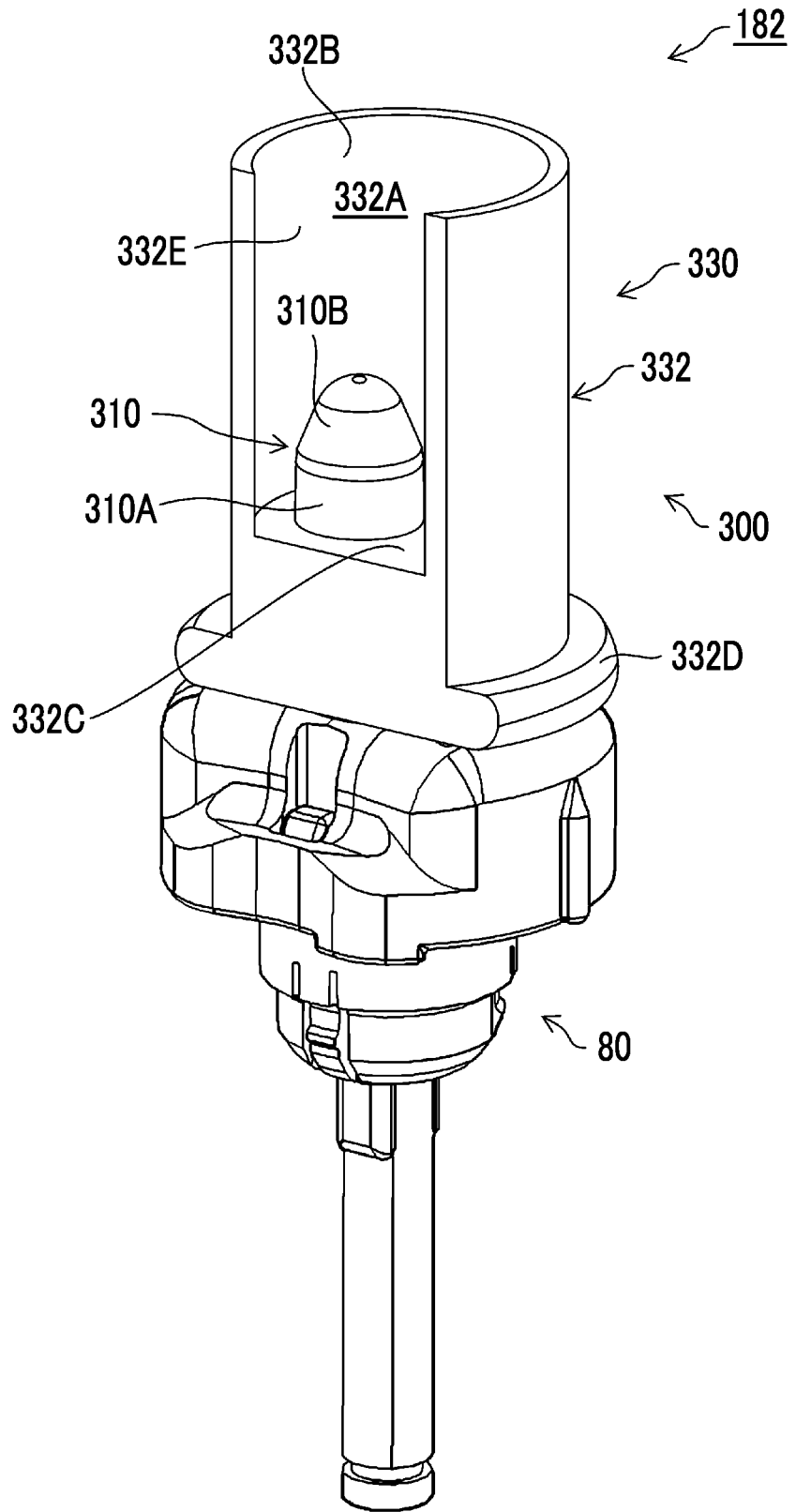
FIG. 15 is a perspective view of a second embodiment of the mounting component.

FIG. 15 is a perspective view of a mounting component 182 of the second embodiment. The mounting component 182 of the second embodiment comprises the wire fixing section 80 and a jig section 300. The configuration of the jig section 300 is different from the configuration of the jig section 200 of the first embodiment. Hereinafter, the configuration of the jig section 300 will be described.

As shown in FIG. 15, the jig section 300 comprises a body portion 310 and a connection portion 330 that is connected to the body portion 310.

The body portion 310 has a shape different from the body portion 202 of the first embodiment. The body portion 310 comprises a cylindrical part 310A and a distal end part 310B that is continuous with the cylindrical part 310A and that becomes tapered as the distal end part 310B becomes farther from the cylindrical part 310A. The distal end part 310B has a substantially conical shape, and the side surface thereof forms an inclined surface that is tapered in the direction of insertion indicated by the arrow. The distal end shape of the distal end part 310B may be a dome shape formed by a curved surface as shown in FIG. 15, a flat surface, or a needle shape that converges to one point as long as the distal end part 310B comprises the inclined surface that is tapered in the direction of insertion.

The connection portion 330 comprises a housing member 332 in which a space 332A housing the distal end cap 34 is formed. The housing member 332 has a first opening 332B that allows housing the distal end cap 34, and a bottom 332C that faces the first opening 332B.

The body portion 310 is connected to the bottom 332C of the housing member 332 at a position opposite to the direction of insertion of the body portion 310. The housing member 332 comprises a flange 332D on the side opposite to the first opening 332B.

The housing member 332 shown in FIG. 15 comprises preferably a second opening 332E facing the side orthogonal to the direction of insertion of the body portion 310. Since the second opening 332E is formed, the housing member 332 has a substantially C-shaped gutter shape in a cross-section taken along a direction orthogonal to the direction of insertion.

In the jig section 300, the connection of the body portion 310 and the connection portion 330 includes a case where the body portion 310 and the connection portion 330 are integrally molded and a case where the body portion 310 and the connection portion 330 are formed as separate members and are bonded to each other using an adhesive or the like.

The jig section 300 may be made of the same material as in the first embodiment.

FIGS. 16A and 16B are perspective views showing a procedure for detaching the distal end cap using the second embodiment of the mounting component 182. FIG. 16A is a perspective view showing a state before the jig section 300 is inserted into the distal end cap 34, and FIG. 16B is a perspective view showing a state after the jig section 300 is inserted into the distal end cap 34.

As shown in FIG. 16A, the mounting component 182 detached from the proximal operation part 22 is prepared. The position of the mounting component 182 is adjusted with respect to the distal end cap 34 in a direction in which the tapered part of the body portion 310 of the jig section 300 faces the distal end opening 34C and at least the inclined surface included in the distal end part 310B comes into contact with the wall 34A. The jig section 300 is disposed in a state in which the first opening 332B of the housing member 332 faces the distal end cap 34 side and the second opening 332E of the housing member 332 faces the Z(+) side. As in the first embodiment, the elevator housing space 66 and the inner space 34E of the distal end cap 34 substantially coincide with each other.

As shown in FIG. 16B, the distal-end-portion body 32 on which the distal end cap 34 is mounted is housed in the space 332A of the housing member 332, and the body portion 310 is inserted into the inner space 34E of the distal end cap 34 through the distal end opening 34C. For example, the body portion 310 is pushed into the inner space 34E of the distal end cap 34 while the housing member 332 is held by a finger or the like.

The diameter of the inclined surface included in the distal end part 310B increases in the direction opposite to the direction of insertion. The outer diameter of the distal end part 310B formed by the inclined surface at a certain position is larger than the distance between the partition wall 68 and the wall 34A positioned on the X(+) side with respect to the partition wall 68.

As the body portion 310 is inserted into the inner space 34E of the distal end cap 34, the inclined surface of the distal end part 310B pushes the wall 34A in the direction (X(+) direction) of expanding the inner space 34E of the distal end cap 34, to deform the distal end cap 34. The deformation of the distal end cap 34 facilitates the detachment of the distal end cap 34 from the distal-end-portion body 32. Damage to the observation window 76 of the distal-end-portion body 32 can be suppressed.

In FIG. 16B, the operator can visually recognize the deformed state of the distal end cap 34 through the second opening 332E of the housing member 332.

Further, the deformation of the distal end cap 34 facilitates the release of the engaged stopped portion 150B and stopper portions 160.

Further, since the first cut 34F and the second cut 34G are formed in the distal end cap 34, the wall 34A can be easily deformed.

The distal end cap 34 detached from the distal-end-portion body 32 is discarded without being reused.

Figure 17:
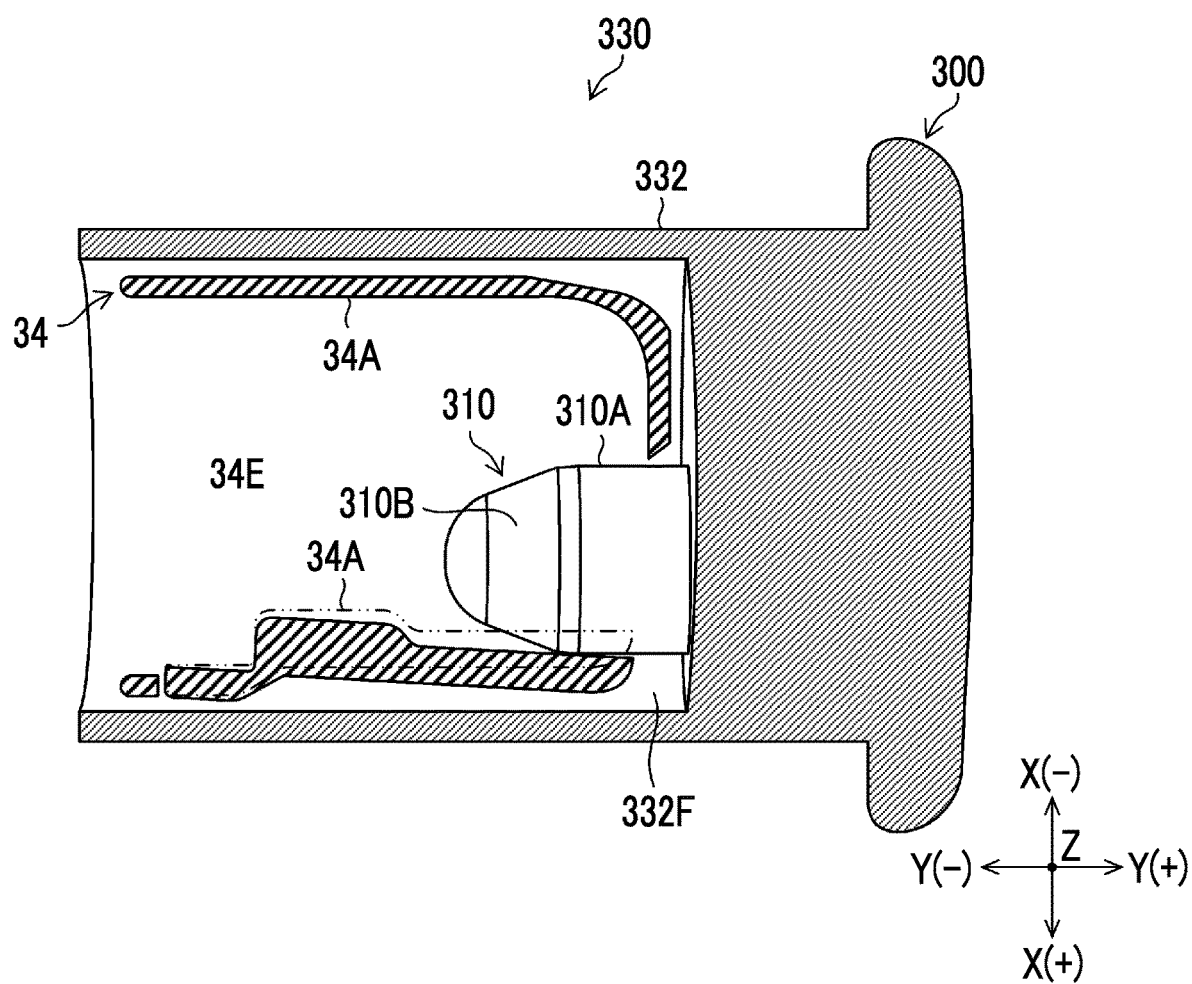
FIG. 17 is a cross-sectional view of a jig section of the mounting component of the second embodiment in a state in which the jig section is inserted into the distal end cap.

FIG. 17 is a cross-sectional view that is taken along a plane parallel to the X-axis direction and the Y-axis direction and passing through the substantially center of the body portion 310, in the state of FIG. 16B. In FIG. 17, the wire fixing section 80 is omitted. As shown in FIG. 17, when the body portion 310 is inserted into the inner space 34E of the distal end cap 34, the inclined surface of the distal end part 310B pushes the wall 34A in the X(+) direction to deform the distal end cap 34.

In order to make the distal end cap 34 deformable, the space 332A has a size in which the space 332A includes an escape space 332F between the wall 34A of the distal end cap 34 and the interior wall of the housing member 332.

Third Embodiment

A mounting component of a third embodiment will be described with reference to FIGS. 18 and 19. The same reference numerals may be given to the same configurations as those of the first and second embodiments, and the description thereof may be omitted.

Figure 18:
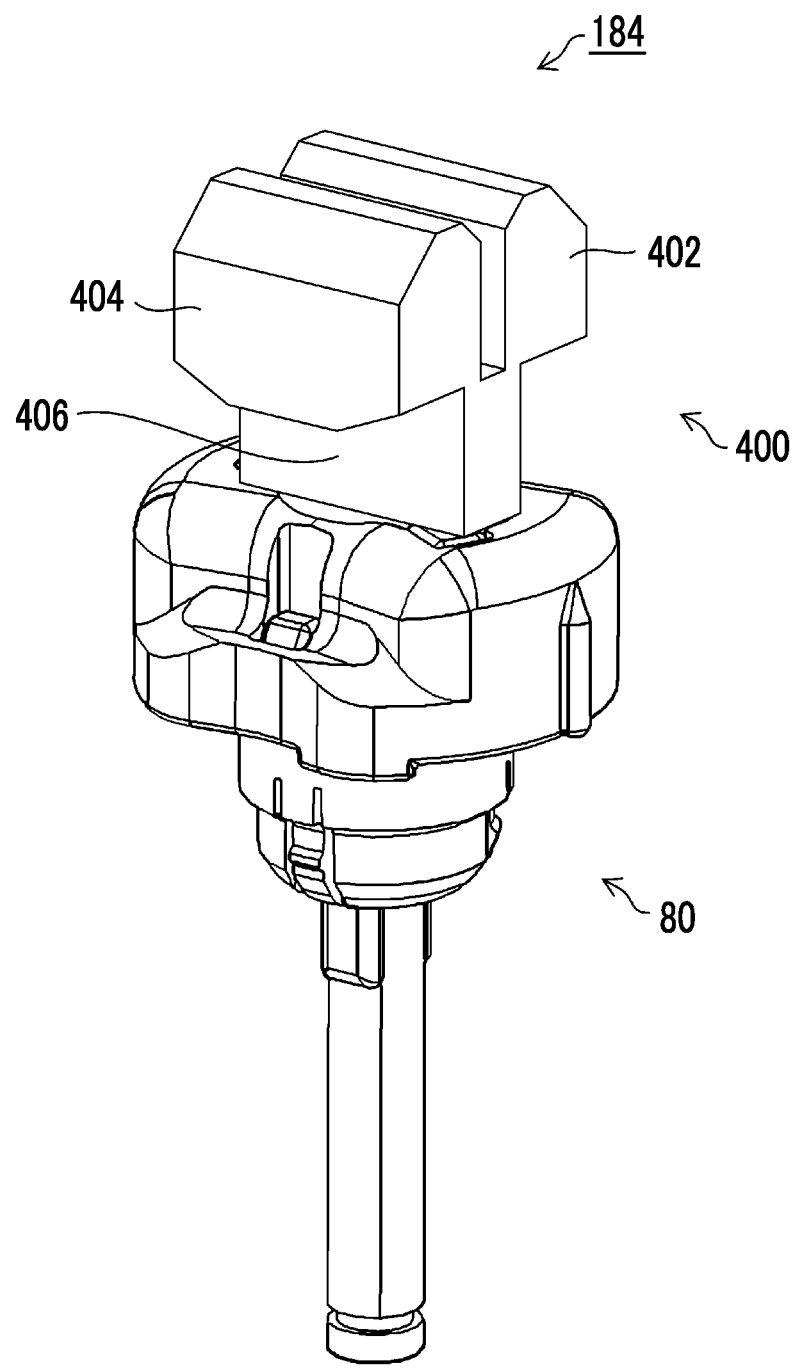
FIG. 18 is a perspective view of a mounting component according to a third embodiment.

FIG. 18 is a perspective view of a mounting component 184 of the third embodiment. The mounting component 184 of the third embodiment comprises the wire fixing section 80 and a jig section 400. The configuration of the jig section 400 is different from the configuration of the jig section 200 of the first embodiment and the jig section 300 of the second embodiment. Hereinafter, the configuration of the jig section 400 will be described.

As shown in FIG. 18, the jig section 400 has two wall members 402 and 404 that are spaced apart and arranged to face each other. In the embodiment, a support member 406 that supports the two wall members 402 and 404 is provided. The two wall members 402 and 404 and the support member 406 are integrally molded. The support member 406 is connected to the wire fixing section 80. The wall members 402 and 404 are spaced apart from each other by at least a distance at which the wall 34A of the distal end cap 34 can be inserted. The two wall members 402 and 404 each have a substantially rectangular parallelepiped shape.

The jig section 400 can be made of the same material as in the first embodiment.

Figure 19:
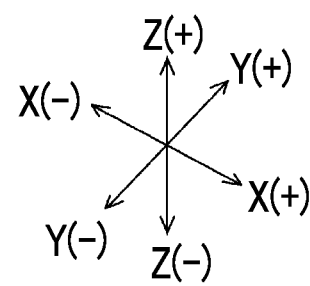
FIG. 19 is a diagram showing a procedure for detaching the distal end cap using the third embodiment of the mounting component.

FIG. 19 is a perspective view showing a procedure for detaching the distal end cap using the third embodiment of the mounting component 184.

First, the mounting component 184 detached from the proximal operation part 22 is prepared. Next, the wall members 402 and 404 of the jig section 400 of the mounting component 184 are directed toward the distal end cap 34 side. The mounting component 184 is positioned so that the gap between the wall members 402 and 404 is parallel to the wall 34A of the distal end cap 34.

As shown in FIG. 19, one wall member 404 is inserted into the inner space 34E of the distal end cap 34 through the cap opening 34B. The other wall member 402 is disposed at a position facing the wall member 404 with the wall 34A interposed therebetween. The wall member 402 is positioned outside the distal end cap 34. A part of the wall 34A of the distal end cap 34 is inserted between the wall members 402 and 404.

As shown by the arrow, the jig section 400 is rotated around the axis of the major axis direction Ax of the insertion part. In the embodiment, the jig section 400 is rotated clockwise when viewed from the proximal end side to the distal end side to apply a force to a part of the wall 34A of the distal end cap 34. The jig section 400 deforms the distal end cap 34 in the direction of expanding the inner space 34E of the distal end cap 34. The deformation of the distal end cap 34 facilitates the detachment of the distal end cap 34 from the distal-end-portion body 32. In the third embodiment, since the fracture mode of the first cut 34F and the second cut 34G is shear, the wall 34A can be made thicker as compared with the first and second embodiments, and the rigidity at the time of use can be ensured.

In FIG. 19, the operator can easily visually recognize the deformed state of the distal end cap 34.

Further, the deformation of the distal end cap 34 facilitates the release of the engaged stopped portion 150B and stopper portions 160.

Further, since the first cut 34F and the second cut 34G are formed in the distal end cap 34, the wall 34A can be easily deformed.

The distal end cap 34 detached from the distal-end-portion body 32 is discarded without being reused.

The first to third embodiments of the mounting components include the wire fixing section and the jig section. It is possible to make the operator comply with the release of the fixing of the wire before the operator detaches the distal end cap. With the jig section, the distal end cap can be easily detached.

EXPLANATION OF REFERENCES

10: endoscope
12: endoscope system
14: endoscope processor apparatus
15: light source device
15A: processor-side connector
16: image processing device
18: display
20: elevating operation lever
22: proximal operation part
24: insertion part
26: soft portion
28: bendable portion
30: distal end portion
32: distal-end-portion body
34: distal end cap
34A: wall
34B: cap opening
34C: distal end opening
34D: mounting opening
34E: inner space
34F: first cut
34G: second cut
36: treatment tool elevator
37: treatment tool channel
38: elevating operation wire
40: wire channel
42: air/water supply tube
44: cable insertion channel
46: operation-part body
48: grip portion
50: bending-proof pipe
52: universal cable
54: connector device
57: air/water supply button
58: air/water supply nozzle
59: suction button
60: treatment tool outlet port
61: through-hole
62: angle knob
64: treatment tool inlet port
66: elevator housing space 68: partition wall
68A: upper surface
74: illumination window
76: observation window
80: wire fixing section
82: sliding member
82A: groove
82B: engaging portion
82C: snap restriction member
82D: screw portion
82E: tapered surface
84: holding member
84A: snap
84B: claw
84C: notch
86: wire grip member
86A: tapered surface
86B: slit
88: holding member
88A: member
88B: member
88C: engagement surface
88D: screw portion
90: movement restriction member
92: packing
108: sliding restriction pipe
120: link member
122: rod
124: connection member
124A: protrusion
124B: through-hole
124C: engaged portion
150: cantilever piece
150A: support piece
150B: stopped portion
160: stopper portion
162: groove portion
180: mounting component
182: mounting component
184: mounting component
200: jig section
202: body portion
204: inclined surface
206: inclined surface
208: plane
210: plane
212: plane
300: jig section
310: body portion
310A: cylindrical part
310B: distal end part
330: connection portion
332: housing member
332A: space
332B: first opening
332C: bottom
332D: flange
332E: second opening
332F: escape space
400: jig section
402: wall member
404: wall member
406: support member
Ax: major axis direction

What is claimed is:

1. An endoscope comprising:
an operation part that is provided with an operation member;
an insertion part that is provided on a distal end side of the operation part and is inserted into an object to be examined;
an elevator that is provided in a distal end portion of the insertion part;
a distal end cap that is mounted on the distal end portion and has an inner space communicating with a cap opening;
an elevating operation wire of which a distal end side is connected to the elevator and which is pushed and pulled in response to operation of the operation member to operate the elevator;
a wire channel through which the elevating operation wire is inserted; and
a mounting component that is attachably and detachably mounted on a proximal side of the operation part,
wherein the mounting component has a wire fixing section that mechanically connects the operation member and the elevating operation wire to each other, and a cap detaching tool capable of detaching the distal end cap from the distal end portion,
the wire fixing section is a tubular member having a tubular shape which is along a longitudinal axis direction corresponding to a longitudinal direction of the elevating operation wire, and
the cap detaching tool is connected to one end side of the tubular member in the longitudinal axis direction,
wherein the cap detaching tool has a width tapering in a direction opposite the one end side in the longitudinal axis direction, in a state where the cap detaching tool is connected to the wire fixing section, and
the width of the cap detaching tool is, at least partially, larger than a width of the inner space of the distal end cap.

2. The endoscope according to claim 1,
wherein the cap detaching tool includes: a body portion in which the width tapered is formed; and a connection portion that is connected to the body portion,
the connection portion has a housing member in which a space that houses the distal end cap is formed,
the housing member has: a first opening which is opened in the longitudinal axis direction and whose width is larger than a width of an outer periphery of the distal end cap; and a bottom that faces the first opening, and
the body portion is connected to the bottom on a side opposite to the first opening in the longitudinal axis direction.

3. An endoscope comprising:
an operation part that is provided with an operation member;
an insertion part that is provided on a distal end side of the operation part and is inserted into an object to be examined;
an elevator that is provided in a distal end portion of the insertion part;
a distal end cap that is mounted on the distal end portion and has an inner space communicating with a cap opening;
an elevating operation wire of which a distal end side is connected to the elevator and which is pushed and pulled in response to operation of the operation member to operate the elevator;

a wire channel through which the elevating operation wire is inserted; and a mounting component that is attachably and detachably mounted on a proximal side of the operation part, wherein the mounting component has a wire fixing section that mechanically connects the operation member and the elevating operation wire to each other, and a cap detaching tool capable of detaching the distal end cap from the distal end portion, the wire fixing section is a tubular member having a tubular shape which is along a longitudinal axis direction corresponding to a longitudinal direction of the elevating operation wire, and the cap detaching tool is connected to one end side of the tubular member in the longitudinal axis direction, wherein the cap detaching tool has two wall members that are spaced apart and arranged to face each other; and a gap formed between the two wall members, at least one of the two wall members has a thickness which allows the at least one of the two wall members to be inserted into the inner space of the distal end cap, the distal end cap has at least one wall, and the gap between the two wall members of the detaching tool is larger than a thickness of the at least one wall of the distal end cap.

4. A mounting component that is attachably and detachably mounted on an operation part of an endoscope, the mounting component comprising:

a wire fixing section; and a cap detaching tool, wherein the wire fixing section connects an elevating operation wire of which a distal end side is connected to an elevator provided in a distal end portion of an insertion part of the endoscope and an operation member provided in the operation part to each other, the cap detaching tool is a section that is used to detach a distal end cap mounted on a distal end portion of the endoscope and having an inner space communicating with a cap opening, from the distal end portion, the wire fixing section is a tubular member having a tubular shape which is along a longitudinal axis direction corresponding to a longitudinal direction of the elevating operation wire, and the cap detaching tool is connected to one end side of the tubular member in the longitudinal axis direction, wherein the cap detaching tool has a width tapering in a direction opposite the one end side in the longitudinal axis direction, in a state where the cap detaching tool is connected to the wire fixing section, and the width of the cap detaching tool is, at least partially, larger than a width of the inner space of the distal end cap.

5. The mounting component according to claim 4, wherein the cap detaching tool includes: a body portion in which the width tapered is formed; and a connection portion that is connected to the body portion, the connection portion has a housing member in which a space that houses the distal end cap is formed, the housing member has: a first opening which is opened in the longitudinal axis direction and whose width is larger than a width of an outer periphery of the distal end cap; and a bottom that faces the first opening, and the body portion is connected to the bottom a side opposite to the first opening in the longitudinal axis direction.

6. A mounting component that is attachably and detachably mounted on an operation part of an endoscope, the mounting component comprising:

a wire fixing section; and a cap detaching tool, wherein the wire fixing section connects an elevating operation wire of which a distal end side is connected to an elevator provided in a distal end portion of an insertion part of the endoscope and an operation member provided in the operation part to each other, the cap detaching tool is a section that is used to detach a distal end cap mounted on a distal end portion of the endoscope and having an inner space communicating with a cap opening, from the distal end portion, the wire fixing section is a tubular member having a tubular shape which is along a longitudinal axis direction corresponding to a longitudinal direction of the elevating operation wire, and the cap detaching tool is connected to one end side of the tubular member in the longitudinal axis direction, wherein the cap detaching tool has two wall members that are spaced apart and arranged to face each other; and a gap formed between the two wall members, at least one of the two wall members has a thickness which allows the at least one of the two wall members to be inserted into the inner space of the distal end cap, the distal end cap has at least one wall, and the gap between the two wall members of the detaching tool is larger than a thickness of the at least one wall of the distal end cap.

7. The endoscope according to claim 1, further comprising a link member disposed outside the operation part, wherein, in a case where the mounting component is mounted on the proximal end side of the operation part, the wire fixing section of the mounting component is partially housed on a proximal end side of the link member.

8. The endoscope according to claim 7, wherein the link member comprises a rod configured to be connected to the operation member.

9. The mounting component according to claim 4, further comprising a link member disposed outside the operation part, wherein, in a case where the mounting component is mounted on the proximal end side of the operation part, the wire fixing section of the mounting component is partially housed on a proximal end side of the link member.

10. The mounting component according to claim 9, wherein the link member comprises a rod configured to be connected to the operation member.

* * * * *